US011878292B2

(12) United States Patent
Jan et al.

(10) Patent No.: US 11,878,292 B2
(45) Date of Patent: Jan. 23, 2024

(54) MFI ZEOLITE AND ITS USES FOR PRODUCTION OF LIGHT OLEFINS AND/OR AROMATICS

(71) Applicant: UOP LLC, Des Plaines, IL (US)

(72) Inventors: Deng-Yang Jan, Elk Grove Village, IL (US); Jaime G. Moscoso, Mount Prospect, IL (US); Lijun Xu, Schaumburg, IL (US); Xi Zhao, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 18/176,459

(22) Filed: Feb. 28, 2023

(65) Prior Publication Data

US 2023/0278016 A1    Sep. 7, 2023

Related U.S. Application Data

(60) Provisional application No. 63/315,480, filed on Mar. 1, 2022.

(51) Int. Cl.
| | | |
|---|---|---|
| *C07C 1/24* | (2006.01) | |
| *B01J 29/40* | (2006.01) | |
| *C07C 4/06* | (2006.01) | |
| *B01J 37/10* | (2006.01) | |
| *B01J 35/10* | (2006.01) | |

(52) U.S. Cl.
CPC ........... *B01J 29/40* (2013.01); *B01J 35/1019* (2013.01); *B01J 35/1038* (2013.01); *B01J 37/105* (2013.01); *C07C 1/24* (2013.01); *C07C 4/06* (2013.01); *C07C 2529/40* (2013.01)

(58) Field of Classification Search
CPC .... B01J 29/40; B01J 35/1019; B01J 35/1038; B01J 37/105; C07C 1/24; C07C 4/06; C07C 2529/40
See application file for complete search history.

(56) References Cited

U.S. PATENT DOCUMENTS 4,257,885 A    3/1981  Grose et al.
4,822,939 A *  4/1989  Chu .......................... C07C 1/20
                                                585/408

(Continued)

FOREIGN PATENT DOCUMENTS

| CN | 101898767 A | 12/2010 |
| CN | 102259013 A * | 11/2011 |
| JP | 1993070616 B2 | 10/1993 |

OTHER PUBLICATIONS

G. Kresse, "Ab initio molecular dynamics for liquid metals", Jan. 1, 1993.

(Continued)

*Primary Examiner* — Youngsul Jeong
*Assistant Examiner* — Jason Y Chong
(74) *Attorney, Agent, or Firm* — Paschall & Associates, LLC; James C. Paschall

(57) ABSTRACT

An improved MFI zeolite having low aluminum occupation at intersection sites characterized by an ortho-xylene to para-xylene uptake ratio of 0.1 to about 0.55. Processes for converting hydrocarbon or oxygenate to a product comprising light olefins and/or aromatics using the improved MFI zeolite as catalyst are also disclosed. Para-xylene in the product may be greater than about 24% of the xylenes.

7 Claims, 17 Drawing Sheets

(56) References Cited

U.S. PATENT DOCUMENTS

| | | | |
|---|---|---|---|
| 7,488,700 B2 | 2/2009 | Choi et al. | |
| 9,809,505 B1* | 11/2017 | Buchanan | C07C 1/20 |
| 9,926,240 B2* | 3/2018 | Ward | B01J 35/0006 |
| 11,358,912 B2 | 6/2022 | Miller et al. | |

OTHER PUBLICATIONS

G. Kresse, "Efficiency of ab-initio total energy calculations for metals and semiconductors using a plane-wave basis set", 1996, Publisher: Elsevier Science B.V.

Claire T. Nimlos, "Experimental and Theoretical Assessments of Aluminum Proximity in MFI Zeolites and Its Alteration by Organic and Inorganic Structure-Directing Agents", Oct. 20, 2020, Publisher: American Chemical Society.

G. Kresse, "From ultrasoft pseudopotentials to the projector augmented-wave method", Jan. 15, 1999, Publisher: The American Physical Society.

John P. Perdew, "Generalized Gradient Approximation Made Simple", 10/28/21996, Publisher: The American Physical Society.

Graeme Henkelman, "Improved tangent estimate in the nudged elastic band method for finding minimum energy paths and saddle points", Dec. 8, 2000, Publisher: American Insitute of Physics.

Young Gul Hur, "Influence of Tetrapropylammonium and Ethylenediamine Structure-Directing Agents on the Framework Al Distribution in BAIMFI Zeolites", Jun. 10, 2019, Publisher: American Chemical Society.

Stefan Grimme, "Semiempirical GGA-Type Density Functional Constructed with a Long-Range Dispersion Correction", Sep. 5, 2006, Publisher: Wiley Periodicals, Inc.

R. E. Yakovenko, "Effects of Si02/ Al203 Ratio in ZSM-5 Zeolite on the Activity and Selectivity of a Bifunctional Cobalt Catalyst for Synthesis of Low-Pour-Point Diesel Fuels from CO and H2", Feb. 24, 2022, Publisher: Petroleum Chemistry.

Satoshi Inagaki, "Facile Fabrication of ZSM5 Zeolite Catalyst with High Durability to Coke Formation during Catalytic Cracking of Paraffins", Dec. 10, 2012, Publisher: American Chemical Society Publications.

Sen Wang, "Relation of Catalytic Performance to the Aluminum Siting of Acidic Zeolites in the Conversion of Methanol to Olefins, Viewed via a Comparison between ZSM5 and ZSM-11", May 4, 2018, Publisher: American Chemical Society Publications.

Search Report and Written Opinion for PCT/US2023/063484 dated Jun. 23, 2023.

* cited by examiner

MFI ZEOLITE AND ITS USES FOR PRODUCTION OF LIGHT OLEFINS AND/OR AROMATICS

CROSS-REFERENCE TO RELATED APPLICATIONS

This application claims priority from U.S. Provisional Application No. 63/315,480, filed Mar. 1, 2022, which is incorporated herein in its entirety.

FIELD

The field is zeolites of the MFI structure type having low aluminum occupation at intersection sites and uses in conversion processes.

BACKGROUND

MFI zeolite is versatile in carrying out a wide array of catalytic processes for petrochemical production such as converting oxygenates to light olefins (methanol to hydrocarbons or propylene, MTH or MTP, respectively), to aromatics (MTA), to co-produce light olefins and aromatics, converting naphtha to light olefin (catalytic cracking) or vacuum gas oil to gasoline and light olefins in fluid catalytic cracking (FCC). In the aforementioned processes, undesirable products such as methane, ethane and propane are typically co-produced. For example, ethane and propane are formed via bi-molecular reaction pathways such as hydrogen transfers between light olefin and heavier paraffin and naphthene. The bimolecular hydrogen transfer reaction is affected by the active site density and geometric constraints around the active sites, and it is controlled typically via active site density for a given zeolite such as MFI.

Zeolites are a class of crystalline silicates possessing permanent microporosity based on $TO_{4/2}$ tetrahedra, where T is typically an aluminum or a silicon atom. Replacement of a silicon atom by an aluminum in a T site produces a negative framework charge balanced by a proton or other cation, creating an active site. The locations of the T atoms are unique for each framework and are often referred to as T-sites. As used herein, zeolites may be referred to by an improper name, such as silicalite, a proper name, such as ZSM-5, or by a structure type code, such as MFI. These three letter codes indicate atomic connectivity and hence pore size, shape and connectivity for the various known zeolites. The lists of these codes may be found in the Atlas of Zeolite Framework Types, which is maintained by the International Zeolite Association Structure Commission at http://www.iza-structure.org/databases/. At present, 255 structure types are known and catalogued by the IZA. One such structure type, MFI is described as comprising 3-dimensional 10-ring channels with straight channels along crystallographic axis b and tortuous channels along axis a. Zeolites are distinguished from each other on the basis of their composition, crystal structure, and adsorption properties. One method commonly used in the art to distinguish zeolites is x-ray diffraction.

In addition to converting feed molecules to olefins, inter-olefin conversions should efficiently convert heavy olefins to lighter olefins by finding means to maximize ethylene, propylene, and/or propylene plus ethylene combined. Efficient and selective inter-olefin conversions are needed in converting butenes, light and heavy catalytic naphtha cracking (LCN and HCN) streams derived from FCC of VGO, and in converting $C_4^+$ olefins coming off a methanol to olefin (MTO) process through inter-conversion processes such as an olefin cracking process (OCP). In the aforementioned processes, zeolite catalysts repetitively swing between process and regeneration cycles. In the process cycle, the carbonaceous materials deposit on the catalyst, causing catalyst deactivation. The deactivated catalyst is regenerated to restore the activity typically via a carbon burn procedure, before returning to process cycles. During cycles of process and regeneration, zeolite is exposed to hydrothermal environments (particularly in regeneration), causing the degradation of zeolite acidity via de-alumination processes, where aluminum leaves the framework location, and thus loses of catalytic activity. To maintain the production throughput, the process would require constant make-up of fresh catalysts or progressively more severe reaction conditions after each regeneration cycle. Consequently, the economics of operating the processes would be adversely impacted due to the cost of constant fresh catalyst make-up or total catalyst replacement. In some cases, the rate of fresh catalyst make-up or frequency of replacement is too high to make the process economically viable.

Study of the crystallographic distributions of framework aluminum sites and its impact on zeolitic catalysis is a complex and active area of improvement for MFI zeolite. Literature indicates the majority of aluminum sites are located at the channel intersections for MFI zeolites made using tetra-propylammonium (TPA) structure directing agents (SDAs).

Crystal size and shape is also important. Increased conversion of butene and selectivity to propylene was observed for small MFI crystallites of a square crystallite shape and intergrowth on (0, 1, 0) plane of coffin-shape zeolite crystallites give lower aromatics selectivity due to blockages of straight channel pore mouths and thus higher proportions of sinusoidal channel openings. JP 2011-73913 A shows via direct synthesis of MFI with high crystallization indices, rates of de-alumination are slowed down based on acidity measurements and catalytic tests across the hydrothermal treatments.

Various modifications have been utilized. In WO 2007/043742, modification via incorporating metal phosphate compound onto MFI zeolite slowed the rate of zeolite de-alumination as characterized by the retention of H-NMR signal after the hydrothermal stability treatment. Modification improved stability for catalytic naphtha cracking to olefins. Others have incorporated phosphorus on H-ZSM-5 for the conversion of methanol and obtained catalysts which switched from aromatics to olefin production modes with increasing phosphorus and with xylene products being significantly rich in para-xylene. However, significant decreases in methanol conversion activities and stability as well as micropore volume and surface area were observed.

Thus, there is a need for an improved MFI zeolite for the catalytic production of light olefins and/or aromatics with high conversion, selectivity to the desired product(s), and high selectivity to para-xylene.

BRIEF SUMMARY

We have found that zeolites of the MFI structure type having low aluminum occupation at intersection sites characterized by an ortho-xylene to para-xylene uptake ratio of greater than 0.1 and less than about 0.55 possess unique reactivity for conversion of feedstocks comprising hydrocarbon or oxygenate to products comprising light olefins and/or aromatics.

BRIEF DESCRIPTION OF THE DRAWINGS

Page 2 of the Figures shows plots of ethylene and propylene yield as a function of conversion achieved during the paraffin cracking test of the present disclosure. Open squares are achieved over the MFI of Example 1. Open triangles are achieved over the MFI of Comparative Example 1.1.

Page 3 of the Figures shows plots of ethylene and propylene yield as a function of conversion achieved during the paraffin cracking test of the present disclosure. Open squares are achieved over the MFI of Example 3. Open triangles are achieved over the MFI of Comparative Example 3.1. Stars are achieved over the MFI of Comparative Example 3.2.

Page 4 of the Figures show plots of ethylene and propylene yield as a function of conversion achieved during the modified paraffin cracking test of the present disclosure. Open squares are achieved over the MFI of Example 1. Filled circles are achieved over the MFI of Comparative Examples 1.1 or 1.2.

Page 5 of the Figures show plots of the ratio of ethylene to total moles of ethylene, propylene, and butene as a function of the weight percent of ethylene, propylene, and butene achieved during the modified paraffin cracking test of the present disclosure.

On page 6 of the Figures.

Pages 7 and 8 of the Figures show the impact of zeolite silica to alumina molar ratio on heptane cracking results at 482° C. achieved during the modified paraffin cracking test of the present disclosure.

Pages 9 and 10 of the Figures show the impact of zeolite silica to alumina molar ratio on heptane cracking results at 607° C. achieved during the modified paraffin cracking test of the present disclosure.

Page 11 of the Figures are plots of ethylene and propylene yield as a function of time on stream during the methanol conversion test of Example 8 of the present disclosure. Open squares are achieved over the MFI of Example 1. Stars are achieved over the MFI of Comparative Example 1.1.

Page 12 of the Figures are plots of ethylene and propylene yield as a function of time on stream during the methanol conversion test of Example 8 of the present disclosure. Open squares are achieved over the MFI of Example 2. Open triangles are achieved over the MFI of Comparative Example 2.1. Stars were achieved over the MFI of Comparative Example 2.2.

Page 13 of the Figures are plots of ethylene and propylene yield as a function of time on stream during the methanol conversion test of Example 8 of the present disclosure. Open squares are achieved over the MFI of Example 3. Open triangles are achieved over the MFI of Comparative Example 3.1. Stars were achieved over the MFI of Comparative Example 3.2.

Page 14 of the Figures are plots of aromatics yield as a function of time on stream during the methanol conversion test of Example 8 of the present disclosure. Open squares are achieved over the MFI of Example 2. Open triangles are achieved over the MFI of Comparative Example 2.1. Stars were achieved over the MFI of Comparative Example 2.2.

Page 15 of the Figures are plots of aromatics yield as a function of time on stream during the methanol conversion test of Example 8 of the present disclosure. Open squares are achieved over the MFI of Example 3. Open triangles are achieved over the MFI of Comparative Example 3.1. Stars were achieved over the MFI of Comparative Example 3.2.

Page 16 of the Figures are plots of the ratio of para xylene to total xylenes as a function of total xylenes during the methanol conversion test of Example 8 of the present disclosure. Open squares are achieved over the MFI of Example 2. Open triangles are achieved over the MFI of Comparative Example 2.1. Stars were achieved over the MFI of Comparative Example 2.2.

Page 17 of the Figures are plots of the ratio of para xylene to total xylenes as a function of total xylenes during the methanol conversion test of Example 8 of the present disclosure. Open squares are achieved over the MFI of Example 3. Open triangles are achieved over the MFI of Comparative Example 3.1. Stars were achieved over the MFI of Comparative Example 3.2.

DEFINITIONS

Figure 1:
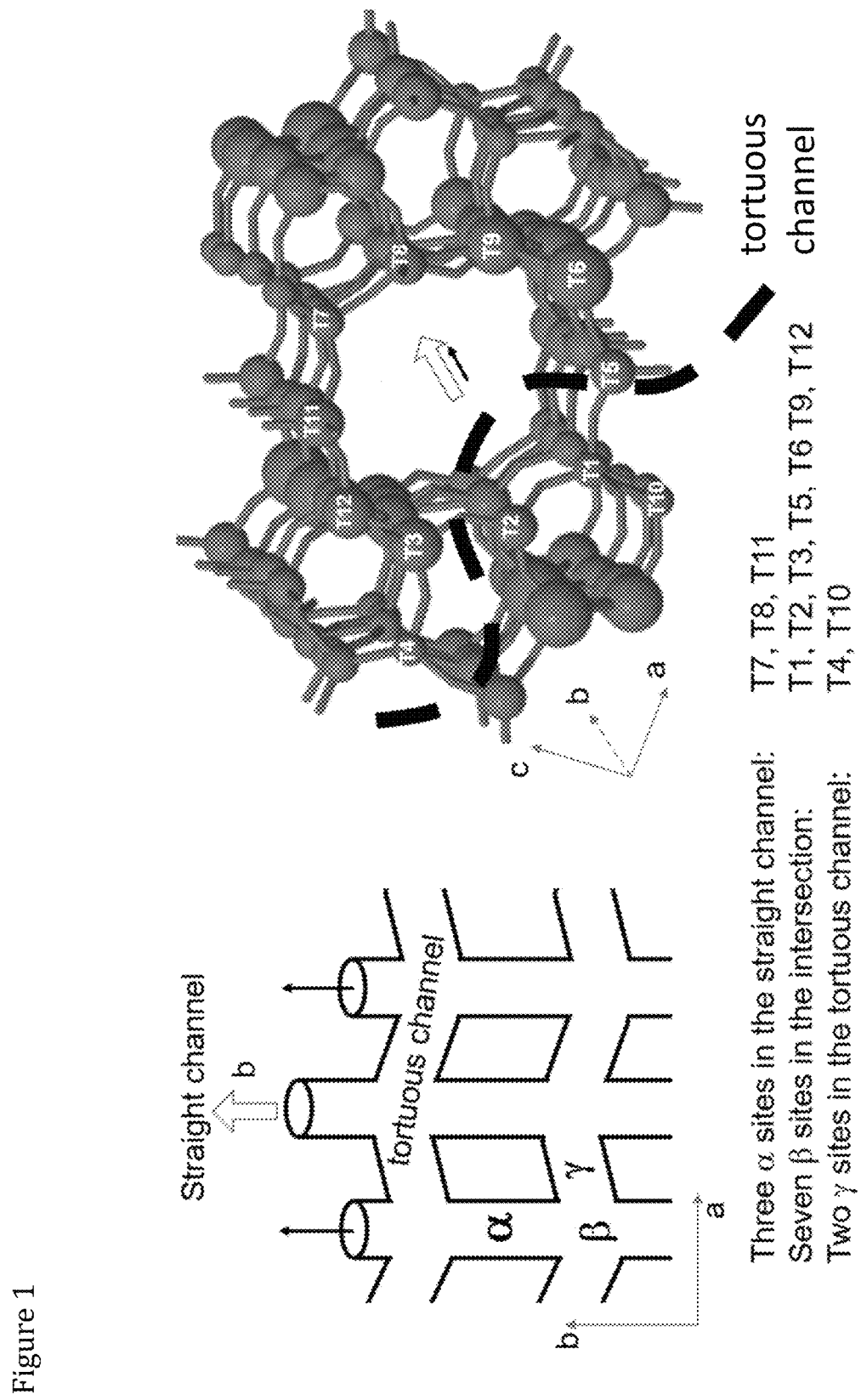
FIG. 1 is a drawing of the MFI zeolite structure. The left side of the figure describes the MFI structure as possessing T-sites in straight channels (alpha), at the channel intersections (beta), and in the tortuous channels (gamma). Straight channels run along the b-axis of the structure. Labeling of the 12 individual T-sites by number is shown on the right side of the figure.
Figure 2:
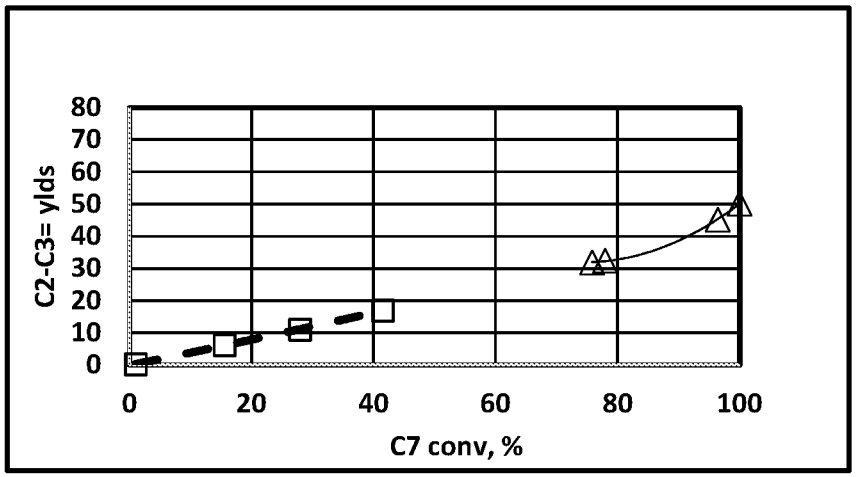
FIG. 2 is the H+ form of the materials.
Figure 3:
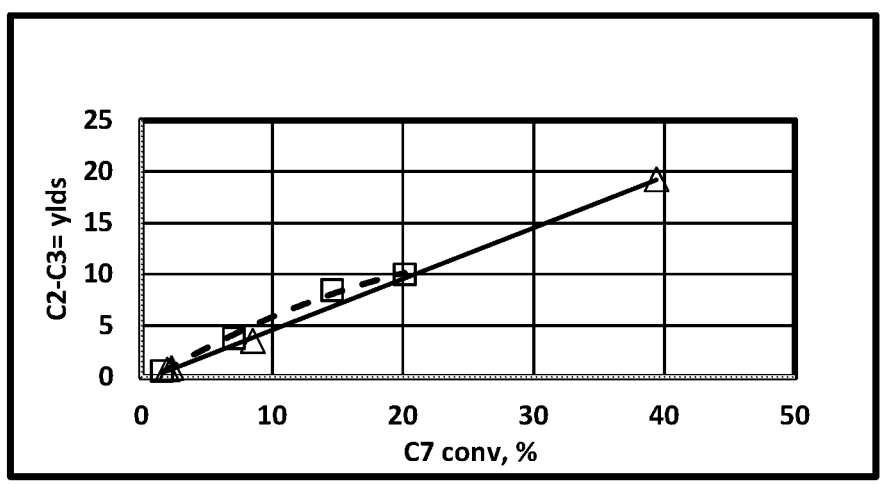
FIG. 3 shows materials steamed at 650° C.
Figure 4:
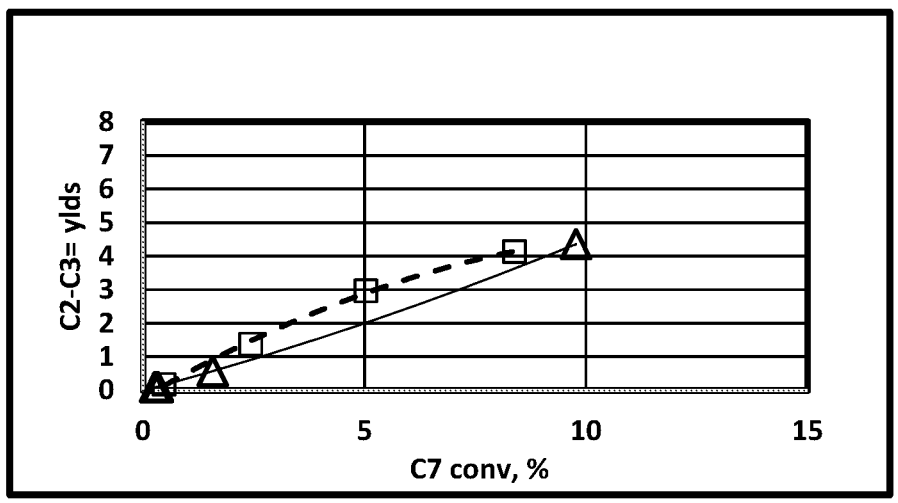
FIG. 4 shows materials after steaming at 760° C.
Figure 5:
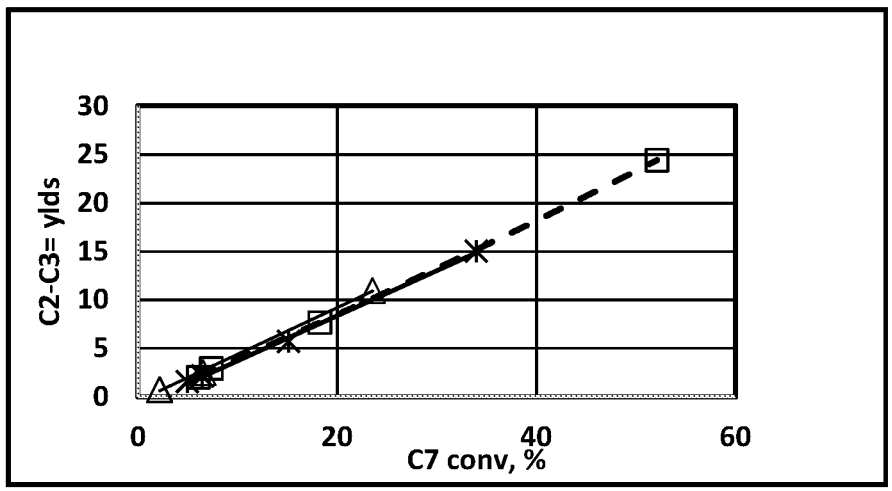
FIG. 5 is the H+ form of the materials.
Figure 6:
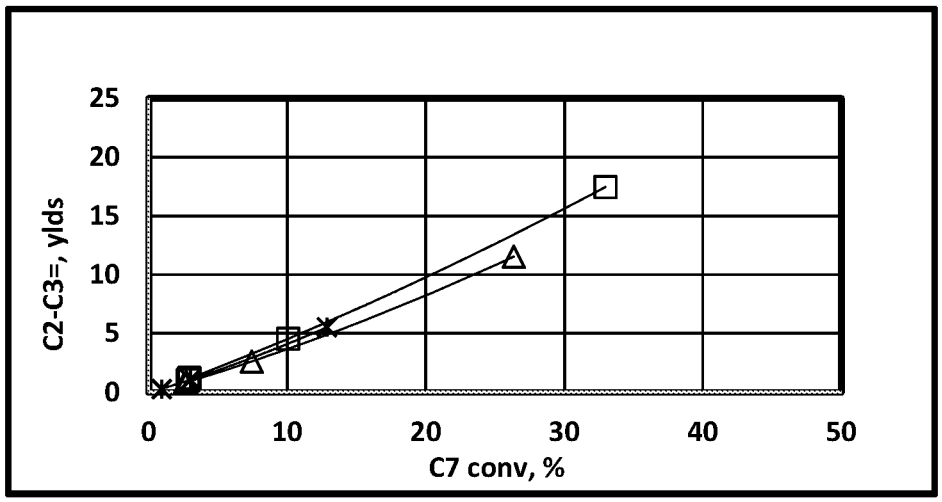
FIG. 6 shows materials steamed at 650° C.
Figure 7:
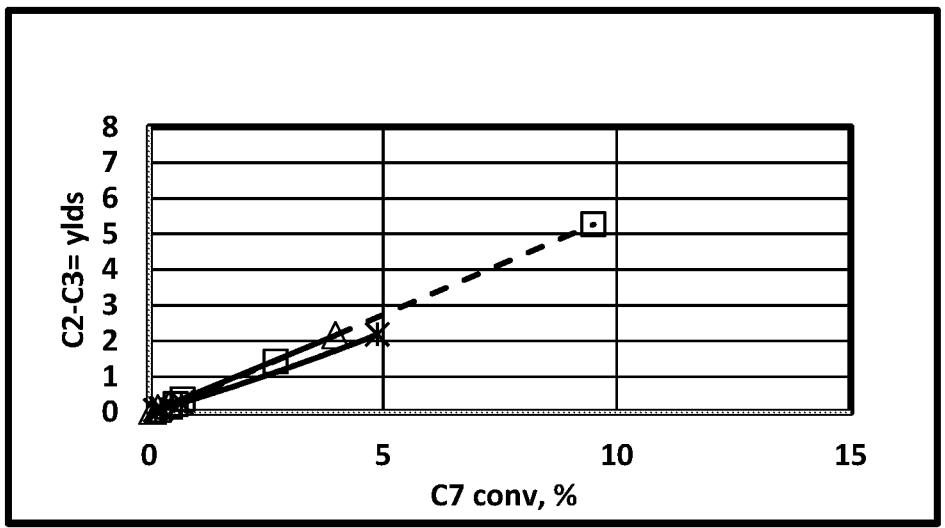
FIG. 7 materials after steaming at 760° C.
Figure 8:
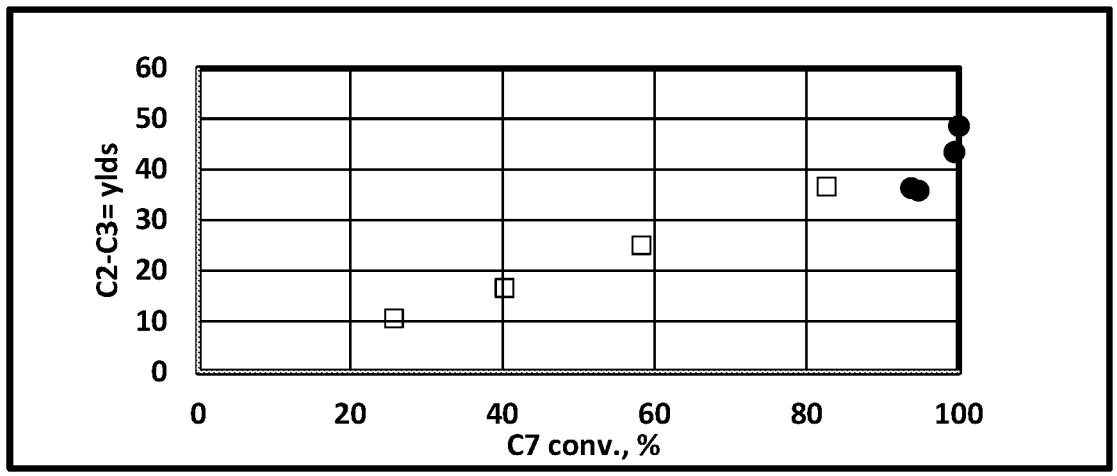
FIG. 8 is the H+ form of the materials, FIG. 9 materials steamed at 650° C.
Figure 9:
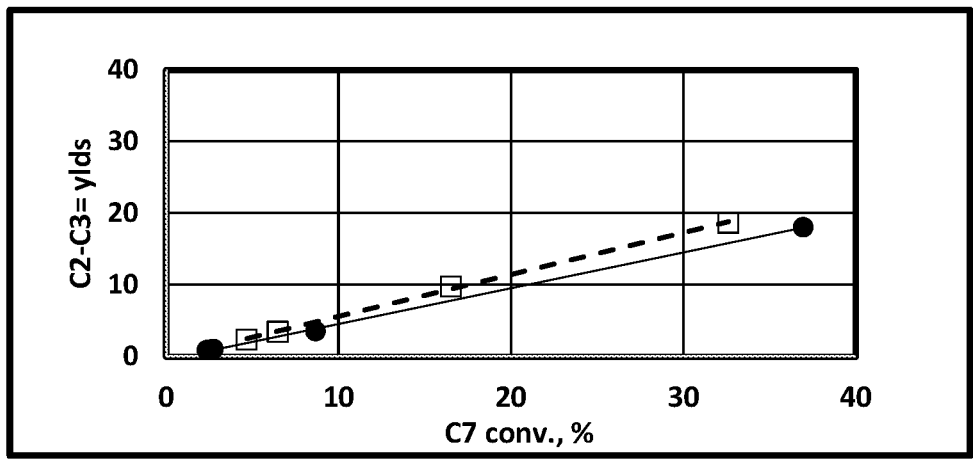
Figure 10:
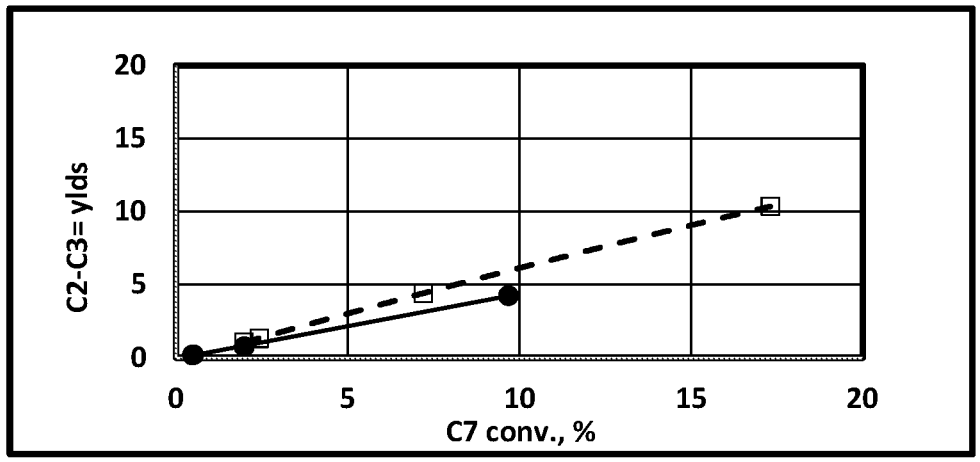
FIG. 10 shows materials after steaming at 760° C.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

As used herein, the term "predominant" or "predominate" or "predominantly" means greater than 50%, suitably greater than 75% and preferably greater than 90%.

The term "Cx" is to be understood to refer to molecules having the number of carbon atoms represented by the subscript "x". Similarly, the term "Cx–" refers to molecules that contain less than or equal to x and preferably x and less carbon atoms. The term "Cx+" refers to molecules with more than or equal to x and preferably x and more carbon atoms.

As used herein, naphtha is to be understood to be a hydrocarbon stream having a boiling point range of from about 25° C. at initial boiling point to about 200° C. at final boiling point. Naphthas may be derived from a variety of sources within a refinery and may potentially be split into multiple fractions all of which are understood to be naphtha. The boiling range for a light naphtha typically ranges from about 29.4° C. (85° F.) at the 5% distillation point to about 82.2° C. (180° F.) at the 95% distillation point by ASTM D-2887. This boiling range encompasses the majority of 2-methylbutane as a key component on the light end and benzene as the key component on the heavy end. Heavy naphtha boiling range may typically be from about 82.2° C. (180° F.) at the 5% distillation point up to about 198.9° C. (390° F.) at the 95% point.

As used herein, the term "gasoline" includes hydrocarbon streams having a T10 boiling point temperature of approximately 70° C. (158° F.) and a T90 boiling point temperature of approximately 190° C. (374° F.).

As used herein, the term "diesel" or "distillate" includes hydrocarbons having a T90 boiling point temperature of approximately 338° C. (640.4° F.) and with an initial boiling point in the range of approximately 150 to approximately 200° C. (302 to 392° F.).

As used herein, the term "vacuum gas oil" (VGO) includes hydrocarbons having an initial boiling point above approximately 343° C. (650° F.), with a T10 boiling point temperature using ASTM D1160 of approximately 370° C. (698° F.) and a T90 boiling point temperature using ASTM D1160 of approximately 500° C. (932° F.).

As used herein, the terms "xylene" or "xylenes" describe the class of dimethyl benzene molecules comprising one or more of 1,2-dimethylbenzene, 1,3-dimethylbenzene, and 1,4-dimethylbenzene. 1,2-dimethylbenzene is often referred to as ortho-xylene or oX. 1,3-dimethylbenzene is often referred to as meta-xylene or mX. 1,4-dimethylbenzene is often referred to as para-xylene or pX.

DETAILED DESCRIPTION

The disclosure provides MFI structure type zeolites characterized by high para-xylene and low ortho-xylene uptake as per measurements by Thermal Gravimetric Analysis (TGA). Unlike conventional MFI, characterized by equilibrium ortho-xylene to para-xylene uptake ratio of 0.70 or higher, this class of MFI exhibits equilibrium ortho-xylene to para-xylene (at 240 minutes) uptake ratio of less than 0.55. The disclosure further provides processes for use of the improved MFI zeolites for conversion of feed streams comprising hydrocarbons or oxygenates to products comprising light olefins and/or aromatics.

In the MFI structure type, adsorption and mass transport takes place primarily along axis b and then permeates through tortuous channels along axis a. The mass transport along the tortuous channels is intrinsically slower than that along straight channels. The mass transport from straight to tortuous channels can be further slowed down by the presence of adsorption sites located at the intersections of straight and tortuous channels. The impact of adsorption sites at intersections on the accessibility to adsorption/active sites in the tortuous channels can be viewed from the effect of framework aluminum densities. The probability of having adsorption sites at the intersections increases as the $SiO_2/Al_2O_3$ ratios decrease (increased numbers of framework aluminum). Specifically, at 46 $SiO_2/Al_2O_3$ ratio, there would be one framework aluminum per intersection, at 94 $SiO_2/Al_2O_3$ half of intersections are occupied by one aluminum, and at 190 $SiO_2/Al_2O_3$, 25% of intersections are occupied by an aluminum assuming adsorption sites are uniformly distributed only among the intersections. The magnitudes of the impact are significantly amplified because reactions taking place at the intersections lead to carbonaceous deposits. Slower mass transport through the blocked intersection reduces the participation of active sites in the tortuous channels as illustrated by the patterns of catalytic performances in responses to $SiO_2/Al_2O_3$ ratios and hydrothermal treatment as illustrated in the examples below.

In this disclosure we tailor the morphology of zeolite MFI independently from altering framework aluminum distributions. The improved MFI zeolite may comprise a heteroatom Q selected from the group consisting of boron, gallium, indium and iron, and mixtures thereof. Incorporation of heteroatom such as boron in addition to framework aluminum may reduce the effective mass transport path across the zeolite following the work by Hur and et. al. in Ind. Eng. Chem. Res. 2019, 58(27), 11849-11860. The heteroatom Q may be boron and the ratio of Si/13 may range from about 2 to about 50. MFI zeolites of the disclosure may be synthesized by incorporating boron and specific organic structural directing agent (OSDA) including ethylenediamine (EDA) and 1,4 diazobicyclo[2.2.2]octane (DABCO) at $SiO_2/Al_2O_3$ ratios ranging from about 60 to about 1000.

This group of MFIs may be synthesized using ethylenediamine (EDA) as the primary structural directing agent (SDA) along with tetra-propylammonium (TPA) as the secondary SDA following the work by Hur mentioned previously and Miller, J. T. and et. al. on WO2019028035A2. This group of MFI's can also be synthesized using DABCO following the procedure described by Nimlos, C. T. and et. al., in Chem. Mater. 2020, 32 (21), 9277-9298. It can also be prepared by the synthesis approach designed by Grose and Flanigen in U.S. Pat. No. 4,257,885.

Improved MFI zeolites of the present disclosure having low aluminum occupation at intersection sites may be synthesized by mixing together a source of silicon, a source of aluminum, a source of boron, a SDA, and water, forming a homogenous mixture of composition comprising these sources, hydrothermally crystallizing the mixture at a temperature of from about 125° C. to about 200° C. or from about 150° C. to about 180° C. while continuously mixing for a time of from about 75 hours to about 100 hours, and recovering a solid product predominantly comprising MFI zeolite.

Silicon, aluminum, and boron sources may be those commonly known in zeolite synthesis including sodium silicate, tetramethyl orthosilicate, tetraethyl orthosilicate, fumed and/or precipitated silica, aluminum nitrate, aluminum hydroxide, sodium aluminate, boron oxide, boric acid and the like.

MFIs of the instant disclosure may also be synthesized via controlling aluminum incorporation rate via using amorphous or crystalline silica alumina as sources of aluminum in molecular sieve syntheses as shown in Tables 2 and 3. A preferred aluminum source is previously crystallized LTA zeolite. The improved MFI zeolite may have a $SiO_2/Al_2O_3$ ratio of from about 60 to about 600 and possess low aluminum occupation at intersection sites characterized by an ortho-xylene to para-xylene uptake ratio of no less than 0.1 and no more than about 0.55. The improved MFI zeolite may be further characterized by a micropore volume as determined by $N_2$ BET of from about 0.11 mL/g to about 0.135 mL/g.

At low $SiO_2/Al_2O_3$ (i.e., $SiO_2/Al_2O_3$) ratios of around 40-50, MFI zeolites with ortho-xylene to para-xylene uptake ratio of between 0.1 and about 0.55 show lower cracking activity and are less stable than MFIs with ortho-xylene to para-xylene uptake ratios of greater than 0.7. However, increasingly higher and more stable paraffin cracking and light olefin yields are observed for MFI zeolites with ortho-xylene to para-xylene uptake ratio of no less than 0.1 and no more than about 0.55 during catalyzed cracking as $SiO_2/Al_2O_3$ increases from 50, to 100 and then to 168 ratios. Calculations on the diffusion and uptake process of ortho-xylene and para-xylene in MFI framework show the change of equilibrium uptake ratio is caused by interactions of xylene molecules with aluminum atoms at different framework locations. Therefore, the adsorption characteristics may suggest a substantial amount of active sites are located in the tortuous channels.

The improved MFI zeolite may also be subjected to hydrothermal and/or steaming treatment to enhance catalytic properties. Hydrothermal conditions may comprise a temperature of from about 500° C. to about 850° C. or from about 600° C. to about 800° C. Hydrothermal conditions may further comprise a steam level of from about 5% to about 100% or from about 20% to about 80%. Steam levels may be calculated for specific temperature, pressure, and diluent compositions from thermodynamic properties of water such as the steam tables. Hydrothermal conditions may further comprise a period of from about 30 minutes to about 24 hours or from about 2 hours to about 18 hours. Following hydrothermal treatment, paraffin cracking activities to olefin may increase and become more stable than those with equilibrium ortho-xylene to para-xylene uptake ratios of greater than 0.7.

Such transition on cracking activity and selectivity after hydrothermal treatment suggests that, without being bound by theory, the adsorption/active sites in the tortuous channels may be more efficient at converting hydrocarbons to olefins (in terms of higher olefin yields and selectivity) and perhaps more hydrothermally stable. It is further noted that distributions among C2-C4 olefins are shifted toward lighter olefin, and most pronouncedly to ethylene, in contrast to conventional MFI zeolites, where ethylene is typically below equilibrium due to significant energetic barriers in olefin interconversions to produce ethylene.

The improved MFI zeolite may be formulated into a catalyst. Forming processes such as extrusion, pelletization, marumerization, oil dropping, and/or spray drying may be used to produce catalysts within specific size and density range to meet fluid dynamic and contact time requirement pertaining to respective processes. The catalyst may comprise zeolite contents of between about 5 and about 80% zeolite or between about 10% and about 50% zeolite. The catalyst may comprise between about 20 and about 95% of binders comprising silica, alumina, magnesia, zirconia, clay and mixtures of thereof. The catalyst may be steam modified prior to use. Steam modification conditions may comprise a temperature in the range of from about 500° C. to about 850° C. and may further comprise a steam level of from about 5% to about 100%, and/or a treatment time in the range of from about 30 minutes to about 24 hours. The catalyst can optionally be modified further via treatment with alkali earth elements, rare earth elements, phosphate, and combinations thereof.

In another embodiment MFI zeolite having less than 0.55 and preferably less than 0.4 oX to pX uptake ratios may be mixed with MFI zeolite having greater than 0.55 oX to pX ratio. In such case, the MFI of low oX to pX ratios may comprise greater than 60% or preferably greater than 70% or most preferably greater than 80% of the total amount of MFI zeolite comprising the catalyst. Catalysts comprising mixtures of MFI zeolites with high and low oX to pX uptake ratios may be formulated into a single formed particle through forming processes previously mentioned. Alternatively, MFI zeolites of low oX/pX and high oX/pX ratios may be in separate formed catalysts following the aforementioned processes before introduction into the hydrocarbon or oxygenate conversion processes. By employing a mixtures of two respective catalyst particles, one can tailor the product compositions, for example, propylene versus ethylene, according to the respective demands at a given time.

Accordingly, an embodiment of the disclosure is a hydrocarbon conversion process comprising contacting a feedstream comprising hydrocarbon with a catalyst wherein the catalyst comprises an improved MFI zeolite comprising in the calcined and ion-exchanged form a molar $SiO_2/Al_2O_3$ ratio of from about 60 to about 600 and having low aluminum occupation at intersection sites characterized by an ortho-xylene to para-xylene uptake ratio of greater than 0.1 and less than about 0.55. The feedstream may be converted to a product at reaction conditions, and a product comprising light olefins, aromatics, or mixtures thereof may be recovered.

Hydrocarbon conversion processes may comprise reactor and/or process designs of fixed bed design, moving beds such as continuous catalyst regeneration (CCR), and/or fluidized beds for converting hydrocarbon feeds to light olefins comprising ethylene and propylene and/or aromatics. The hydrocarbon feed may comprise at least 50 wt % paraffin. The feed may be straight run naphtha or hydrocracked naphtha or catalytically cracked naphtha as are commonly found in refineries. The feed can optionally be hydrotreated to saturate aromatics. In some instances, the feed may contain at least 5 wt % C4+ olefins. The hydrocarbon feed may comprise distillate and/or vacuum gas oil.

Reaction conditions may comprise a pressure of from about 10 to about 3000 kPa, and/or a temperature of from about 500° C. to about 800° C., and/or a WHSV of from about 0.5 to about 25. The feedstream may comprise a diluent selected from the group consisting of nitrogen, steam, methane, hydrogen, and mixtures thereof. The diluent may comprise steam and/or methane. The diluent may comprise steam and/or nitrogen. Diluents may be used to lower the partial pressures of feeds to favor the catalytic cracking to olefin, to introduce the heat required for the endothermic reaction and/or to impart the catalyst sufficient velocity to pass through the reactor section in specific fluidization regions as defined by volumetric catalyst fractions. For fluidized bed hydrocarbon conversion processes, the catalyst to feed ratios (w/w) may be in the range of from about 10 to about 100 and diluent to feed ratios (w/w) may be from about 1 to about 10 or less.

Accordingly, an embodiment of the disclosure is an oxygenate conversion process comprising contacting a feedstream comprising oxygenate with a catalyst. MFI zeolites characterized by ortho-xylene to para-xylene uptake ratios of no less than 0.1 and no more than about 0.55 may comprise the catalyst. Oxygenates may be converted to light olefins (ethylene and propylene) and/or aromatics. Improved relative activity of MFI zeolites of the instant disclosure may increase with increasing $SiO_2/Al_2O_3$ ratios and with hydrothermal treatment versus those of ortho-xylene to para-xylene uptake ratios greater than 0.7, in terms of higher light olefin production and increased stability. Improved catalytic properties may be observed on increasing the $SiO_2/Al_2O_3$ ratio to no greater than about 200 or no greater than about 300, or no greater than about 400 or potentially no greater than 600, and even possibly to no greater than 800. The participation of active sites in the constrained environment (tortuous channels) may be further manifested in higher and stable total aromatics productions, higher xylene and higher para-xylene selectivity out of total xylenes produced.

The oxygenate may comprise methanol, dimethyl ether, dimethyl carbonate, ethanol, and mixtures thereof.

An oxygenate conversion process may comprise passing an oxygenate feedstream to an oxygenate conversion reactor operated at oxygenate conversion reaction conditions, wherein the reactor includes a catalyst, to generate a process stream comprising light olefins and/or aromatics. Oxygenate conversion reaction conditions may comprise a temperature in the range of from about 300° C. to about 600° C. or from about 400° C. to about 500° C., and/or a pressure which allows an absolute oxygenate partial pressure in the range from about 20 kPa to about 800 kPa or from about 100 kPa to about 400 kPa, and/or a WHSV from about 0.1 to about 20 or from about 1 to about 10. The process may further comprise separating the product stream comprising light olefins and/or aromatics into an ethylene stream, a propylene stream, a C4 stream, a C5 stream, a C5+ heavies stream, an aromatics stream, and combinations thereof. Separated portions of the product stream may be used as feed streams for further process units.

The consistently low and slow ortho-xylene uptakes going from 50 to 168 $SiO_2/Al_2O_3$ as shown below, without being bound by theory, suggest the adsorption sites are located in the tortuous channels, where adsorption energetics are not favorable under measurement conditions. Rates of adsorptions can slow down further when the adsorption sites located at the intersections of straight and tortuous channels become occupied after initial uptake of ortho-xylene. This interpretation of experimental observations is corroborated with Density Functional Theory (DFT) calculations. DFT calculated diffusion pathways and energetics indicate, the diffusion barriers from T1 aluminum to T1 aluminum (located at intersections) along the straight channels and from non-aluminum T1 (intersection) to T4 (located in tortuous channel) aluminum sites remain low with orthro-xylene being 24-30 kJ/mol more difficult than para-xylene, see Table 1, FIG. 1 and Table 1 below. However, diffusion barrier for translation of molecules when aluminum is located at T1 site versus aluminum located at the T4 site increase appreciably with ortho-xylene being about 20 kJ/mol higher than para-xylene. Furthermore, when both T1 and T4 sites are occupied with aluminum, diffusion barriers from intersection to tortuous channel are significantly increased for both para-xylene and ortho-xylene with access barrier for ortho-xylene elevated to a level greater than 100 kJ/mol. It suggests that the occupation of T1 by aluminum (located at intersection) would significantly impact the accessibility to a T4 aluminum site in the tortuous channels especially for a bulky molecule such as ortho-xylene, while a less bulky molecule such as para-xylene is not affected. Apparently favorable adsorption at aluminum T1 site makes the diffusion to non-aluminum T4 and aluminum T4 sites a great deal more difficult especially for bulky molecule.

TABLE 1

The MFI crystal structure and definition of the crystallographically unique T sites Cell Symmetry

| Space Group Name H-M | International Tables Number | Setting |
|---|---|---|
| Pnma | 62 | Orthorhombic |

Cell Dimensions (Å)

| 20.0900 | 19.7380 | 13.1420 |
|---|---|---|

Cell Angle (°)

| | | 90 | 90 | 90 |
|---|---|---|---|---|
| | Label | Fractional Coordinate X | Fractional Coordinate Y | Fractional Coordinate Z |
| T-Sites | T1 | 0.4214 | 0.0711 | 0.6898 |
| | T2 | 0.3259 | 0.0336 | 0.8500 |
| | T3 | 0.2792 | 0.0536 | 0.0655 |
| | T4 | 0.1246 | 0.0514 | 0.0481 |
| | T5 | 0.0721 | 0.036 | 0.8233 |
| | T6 | 0.2034 | 0.0687 | 0.7197 |
| | T7 | 0.4195 | 0.8274 | 0.6805 |
| | T8 | 0.3152 | 0.8765 | 0.8361 |
| | T9 | 0.2733 | 0.8278 | 0.0402 |
| | T10 | 0.1185 | 0.8279 | 0.0183 |
| | T11 | 0.0657 | 0.8794 | 0.8087 |
| | T12 | 0.1947 | 0.8288 | 0.7092 |

TABLE 2

Adsorption Energetics and Diffusion Barriers of Para- and Ortho-Xylene in MFI

| | Adsorption (kJ/mol) T1$^\xi$ | Adsorption (kJ/mol) T4$^\xi$ | Adsorption (kJ/mol) T1$^\eta$ | Diffusion barrier (kJ/mol) T1$^\xi$-to-T1$^\xi$ | Diffusion barrier (kJ/mol) T1$^\xi$-through-T4$^\eta$ | Diffusion barrier (kJ/mol) T1$^\xi$-through-T4$^\xi$ | Diffusion barrier (kJ/mol) T1$^\eta$-through-T4$^\xi$ |
|---|---|---|---|---|---|---|---|
| pX | −134 | −102 | −96 | 45 | 71 | 78 | 46 |
| oX | −127 | −96 | −100 | 69 | 89 | 107 | 76 |

($^\xi$T site with Al; $^\eta$T site without Al)

This indicates that para-xylene should have comparable amounts and uptake rates to ortho-xylene, when aluminum occupies T1 sites, consistent with experimental observations for conventional MFI. On the other hand, the diffusion barriers and thus accessibility of ortho-xylene to aluminum T4 site from intersections would depend on whether T1 sites are occupied with aluminum or not. Therefore, the relative adsorption amounts and uptake rate of ortho-xylene to para-xylene are rationalized by distinct aluminum distributions among crystallographic distinct sites.

To enhance the participation of aluminum sites along the tortuous channels and thus improve catalytic performance, one would like to deploy optimized syntheses using choices of SDA, $SiO_2/Al_2O_3$ ratios, and modification methods such as steam, chemical extractions (acid, base or combination) designed to result in adsorption/reaction sites located along the tortuous channels in the gamma position and to have the channel intersections (beta position) void of such sites.

EXAMPLES

Prior to subjecting the samples below to catalytic tests and xylene uptakes by TGA, they were worked up to remove organic SDA and ammonium ion exchanged to lower sodium contents to part per millions on a weight basis. For EDA/TPA-MFI syntheses, the as-synthesized zeolite was first ammonium exchanged four times, each time using 14 ml of 1M $NH_4NO_3$ solution per gram zeolite at 80° C. for 1 hour, and then calcined in a flowing air to lower sodium contents to levels of part per million on a weight basis. As for TPA-MFI samples, the as-synthesized zeolite was first calcined at 580° C. for 6 hours in a flowing air, then ammonium ion exchanged using 25 ml 1 M $NH_4NO_3$ solution per gram zeolite at 80° C., followed by activation.

Example 1

An alumina-boro-silicate solution was prepared by first mixing 43.48 g of aluminum nitrate nonahydrate, 68.11 g boric acid, 66.19 g of ethylenediamine, 29.47 g of TPAOH (40 wt % solution) and 762.07 g of water, while stirring vigorously. After thorough mixing, 430.67 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 90 hours. The solid product was recovered by filtration, washed with de-ionized water, and dried at 100° C. The product was identified as MFI by XRD. Chemical analysis gave a product composition of Si/Al=24.75, Si/B=27.1 The sample was calcined at 580° C. for 6 hours and the BET surface area was 296 m$^2$/g with a micropore volume of 0.119 cc/g and a total pore volume of 0.179 cc/g.

Example 1.2

Example 1.2 was synthesized following the same procedure described for Example 1 but targeting a product Si/Al ratio of 20. The zeolite was analyzed to have 18 Si/Al.

Comparative Example 1.1

An alumina-boro-silicate solution was prepared by first mixing 29.59 g of aluminum nitrate nonahydrate, 46.35 g boric acid, 300.8 g of TPAOH (40% solution), 9.47 g NaOH and 720.7 g of water, while stirring vigorously. After thorough mixing, 293.06 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 72 hours. The solid product was recovered by filtration, washed with de-ionized water, and dried at 100° C. The product was identified as MFI by XRD. Chemical analysis gave a product composition of Si/Al=24.92, Si/B=83.17. The sample was calcined at 580° C. for 6 hours and the BET surface area was 343 $m^2/g$ with a micropore volume of 0.159 cc/g and a total pore volume of 0.212 cc/g.

Comparative Example 1.2

A similar preparation to Example 1.1 was performed with the use of TPAOH as SDA. In this case, the synthesis was performed without boron and yielded MFI-40 as Comparative Example 1.2.

Example 2

An alumina-boro-silicate solution was prepared by first mixing 22.14 g of aluminum nitrate nonahydrate, 69.36 g boric acid, 53.21 g of ethylenediamine, 45.01 g of TPAOH (40% solution) and 771.76 g of water, while stirring vigorously. After thorough mixing, 438.53 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 90 hours. The solid product was recovered by filtration, washed with de-ionized water, and dried at 100° C. The product was identified as MFI by XRD. Chemical analysis gave a product composition of Si/Al=49.91, Si/B=15.99 The sample was calcined at 580° C. for 6 hours and the BET surface area was 301 $m^2/g$ with a micropore volume of 0.124 cc/g and a total pore volume of 0.179 cc/g.

Comparative Example 2.1

An alumina-boro-silicate solution was prepared by first mixing 14.91 g of aluminum nitrate nonahydrate, 46.71 g boric acid, 323.38 g of TPAOH (40% solution) and 719.63 g of water, while stirring vigorously. After thorough mixing, 295.37 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 90 hours. The solid product was recovered by filtration, washed with de-ionized water, and dried at 100° C. The product was identified as MFI by XRD. Chemical analysis gave a product composition of Si/Al=49.67, Si/B=52.6. The sample was calcined at 580° C. for 6 hours and the BET surface area was 355 $m^2/g$ with a micropore volume of 0.129 cc/g and a total pore volume of 0.233 cc/g.

Comparative Example 2.2

MFI-80 was acquired from Zeolyst.

Example 3

An alumina-boro-silicate solution was prepared by first mixing 11.33 g of aluminum nitrate nonahydrate, 70.09 g boric acid, 53.77 g of ethylenediamine, 30.32 g of TPAOH (40% solution) and 791.35 g of water, while stirring vigorously. After thorough mixing, 443.14 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. Chemical analysis gave a product composition of Si/Al=84, Si/B=21.71 The sample was calcined at 580° C. for 6 hours and the BET surface area was 290 $m^2/g$ with a micropore volume of 0.129 cc/g and a total pore volume of 0.165 cc/g.

Comparative Example 3.1

An alumina-boro-silicate solution was prepared by first mixing 7.49 g of aluminum nitrate nonahydrate, 46.91 g boric acid, 324.73 g of TPAOH (40% solution) and 724.27 g of water, while stirring vigorously. After thorough mixing, 296.6 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. Chemical analysis gave a product composition of Si/Al=80.5, Si/B=35.47. The sample was calcined at 580° C. for 6 hours and the BET surface area was 348 $m^2/g$ with a micropore volume of 0.171 cc/g and a total pore volume of 0.195 cc/g.

Comparative Example 3.2

Zeolite silicalite of target $SiO_2/Al_2O_3$ ratio of 95 was synthesized using tetrapropylammonium (TPA) as organic structure directing agent (OSDA). The resulting zeolite after calcination to remove the organic template has Si/Al ratio of 100 and a BET surface area of 358 $m^2/gm$ with a micropore volume of 0.184 cc/g and a total pore volume of 0.208 cc/g.

Example 3.3

An alumina-boro-silicate solution was prepared by first mixing 11.19 g of aluminum nitrate nonahydrate, 70.09 g boric acid, 53.77 g of ethylenediamine, 30.33 g of TPAOH (40% solution) and 791.45 g of water, while stirring vigorously. After thorough mixing, 443.18 g Ludox™ HS-40 ($SiO_2$, mass-40%) was added to the aforementioned mixture. The reaction mixture was homogenized for 20 minutes with a high-speed mechanical stirrer, and then transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. The chemical analysis gave a product composition of $Si/Al_2$=221.47, $Si/B_2$=42.73. The sample was calcined at 580° C. for 6 hrs. and the BET surface area was 287 $m^2/g$ with a micropore volume of 0.143 cc/g and a total pore volume of 0.164 cc/g.

Comparative Example 3.4

An alumina-boro-silicate solution was prepared by first mixing 7.53 g of aluminum nitrate nonahydrate, 47.18 g boric acid, 306.21 g of TPAOH (40% solution) and 740.74 g of water, while stirring vigorously. After thorough mixing, 298.33 g Ludox™ HS-40 ($SiO_2$, mass-40%) was added. The reaction mixture was homogenized for 20 minutes with a high-speed mechanical stirrer, and then transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. The chemical analysis gave a product composition of $Si/Al_2$=186.16, $Si/B_2$=70.15. The sample was calcined at 580° C. for 6 hrs. and the BET surface area was 344 $m^2/g$ with a micropore volume of 0.171 cc/g and a total pore volume of 0.190 cc/g.

Example 3.5

An alumina-boro-silicate solution was prepared by first mixing 5.61 g of aluminum nitrate nonahydrate, 70.31 g boric acid, 53.94 g of ethylenediamine, 30.42 g of TPAOH (40% solution) and 795.15 g of water, while stirring vigorously. After thorough mixing, 444.57 g Ludox™ HS-40 ($SiO_2$, mass-40%) was added. The reaction mixture was homogenized for 20 minutes with a high-speed mechanical stirrer, and then transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. The chemical analysis gave a product composition of $Si/Al_2$=400, $Si/B_2$=40.13. The sample was calcined at 580° C. for 6 hrs and the BET surface area was 273 $m^2/g$ with a micropore volume of 0.137 cc/g and a total pore volume of 0.153 cc/g.

Comparative Example 3.6

An alumina-boro-silicate solution was prepared by first mixing 3.02 g of aluminum nitrate nonahydrate, 47.3 g boric acid, 306.99 g of TPAOH (40% solution) and 743.6 g of water, while stirring vigorously. After thorough mixing, 299.09 g Ludox™ HS-40 ($SiO_2$, mass-40%) was added. The reaction mixture was homogenized for 20 minutes with a high-speed mechanical stirrer, and then transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. The chemical analysis gave a product composition of $Si/Al_2$=441, $Si/B_2$=63.06. The sample was calcined at 580° C. for 6 hrs. and the BET surface area was 342 $m^2/g$ with a micropore volume of 0.173 cc/g and a total pore volume of 0.184 cc/g.

Example 3.7

An alumina-boro-silicate solution was prepared by first mixing 3.74 g of aluminum nitrate nonahydrate, 70.39 g boric acid, 54.0 g of ethylenediamine, 30.45 g of TPAOH (40% solution) and 796.39 g of water, while stirring vigorously. After thorough mixing, 445.03 g Ludox™ HS-40 ($SiO_2$, mass-40%) was added. The reaction mixture was homogenized for 20 minutes with a high-speed mechanical stirrer, and then transferred to a 2-L Parr Hastelloy stir autoclave. The mixture was crystallized at 175° C. with stirring at 300 RPM for 88 hours. The solid product was recovered by filtration, washed with de-ionized water, and dried at 100° C. The product was identified as MFI by XRD. The chemical analysis gave a product composition of $Si/Al_2$=590.6, $Si/B_2$=37.7. The sample was calcined at 580° C. for 6 hrs. and the BET surface area was 285 $m^2/g$ with a micropore volume of 0.144 cc/g and a total pore volume of 0.154 cc/g.

Comparative Example 4

Example 4 follows Example 8 of U.S. Pat. No. 4,257,885 by Grose and Flanigen. It was prepared by using Zeolite silicalite with organic template removed as a seed using a synthesis gel that does not contain organic SDA.

Example 5

In this series, MFI zeolites were synthesized with different ratios of liquid sodium aluminate (LSA) and Linde Type A (LTA) zeolite 4A as an aluminum source.

Example 5.1

An alumina-silicate gel was prepared by first mixing 33.35 g of LTA zeolite (4A), 18.7 g of NaOH, 23.41 g of diethanolamine, 3.95 g of TPABr (50 wt % solution) and 808.96 g of water, while stirring vigorously. After thorough mixing, 502.06 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 160° C. with stirring at 300 RPM for 72 hours. The solid product was recovered by filtration, washed with de-ionized water, and dried at 100° C. The product was identified as MFI by XRD. Chemical analysis gave a product composition of Si/Al=20.31. A small sample was calcined at 580° C.×6 hrs. and the BET surface area was 317 $m^2/g$ with a micropore volume of 0.159 cc/g and a total pore volume of 0.189 cc/g.

The MFI made with LTA was ammonium ion exchanged to exchange Na for $NH_4$. The MFI was ammonium ion-exchanged by contacting 2000 mL of 1 M NH4NHO3 solution with 160 g MFI at 80° C. and stirring for 1 hour, filtered and washed. The procedure was repeated four times.

Example 5.2

An alumina-silicate gel was prepared by first mixing 8.14 g LSA, 33.35 g of LTA zeolite (4A), 17.96 g NaOH, 23.41 g of diethanolamine, 3.95 grs g of TPABr (50% solution) and 813.99 g of water, while stirring vigorously. After thorough mixing, 507.53 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 160° C. with stirring at 300 RPM for 72 hours. The solid product was recovered by filtration, washed with de-ionized water, and dried at 100° C. The product was identified as MFI by XRD. Chemical analysis gave a product composition of Si/Al=20.33. A small sample was calcined at 580° C.×6 hrs and the BET surface area was 327 $m^2/g$ with a micropore volume of 0.16 cc/g and a total pore volume of 0.198 cc/g.

The MFI made was ammonium ion-exchanged following the same procedure as described in (example 5.1)

Comparative Example 5.3

An alumina-silicate gel was prepared by first mixing 16.28 g of liquid sodium aluminate (LSA), 16.67 g of LTA zeolite (4A), 17.95 g of NaOH, 23.4 g of diethanolamine, 3.95 g of TPABr (50% solution) and 808.96 g of water, while stirring vigorously. After thorough mixing, 512.79 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 160° C. with stirring at 300 RPM for 72 hours. The solid product was recovered by filtration, washed with de-ionized water, and dried at 100° C. The product was identified as MFI by XRD. Chemical analysis gave a product composition of Si/Al=20.17. A small sample was calcined at 580° C.×6 hrs. and the BET surface area was 330 m$^2$/g with a micropore volume of 0.159 cc/g and a total pore volume of 0.211 cc/g.

The MFI made was ammonium ion-exchanged following the same procedure as described in (example 5.1)

Comparative Example 5.4

An alumina-silicate gel was prepared by first mixing 24.42 g of liquid sodium aluminate (LSA), 8.33 grs of LTA zeolite (4A), 17.21 g of NaOH, 23.4 g of diethanolamine, 3.95 grs g of TPABr (50% solution) and 808.96 g of water, while stirring vigorously. After thorough mixing, 518.26 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 160° C. with stirring at 300 RPM for 72 hours. The solid product was recovered by filtration, washed with de-ionized water, and dried at 100° C. The product was identified as MFI by XRD. Chemical analysis gave a product composition of Si/Al=19.98. A small sample was calcined at 580° C.×6 hrs. and the BET surface area was 321 m$^2$/g with a micropore volume of 0.157 cc/g and a total pore volume of 0.198 cc/g.

The MFI made was ammonium ion-exchanged following the same procedure as described in example 5.1.

Comparative Example 5.5

An alumina-silicate gel was prepared by first mixing 32.57 g of liquid sodium aluminate (LSA), 16.32 g of NaOH, 23.4 g of diethanolamine, 3.95 grs g of TPABr (50% solution) and 808.96 g of water, while stirring vigorously. After thorough mixing, 523.77 g Ludox HS-40 ($SiO_2$, mass-40%). The reaction mixture was homogenized for 20 minutes with a high-speed mechanical stirrer, transferred to a 2-L Parr Hastelloy stir autoclave. The mixture was crystallized at 160° C. with stirring at 300 RPM for 72 hours. The solid product was recovered by filtration, washed with de-ionized water, and dried at 100° C. The product was identified as MFI by XRD. Chemical analysis gave a product composition of Si/Al=20.17. A small sample was calcined at 580° C.×6 hrs. and the BET surface area was 297 m$^2$/g with a micropore volume of 0.136 cc/g and a total pore volume of 0.239 cc/g.

The MFI made was ammonium ion-exchanged following the same procedure as described in example 5.1.

TABLE 3.1

Composition of MFI made from Zeolite LTA and LSA (Liquid Sodium Aluminate).

| Examples | LTA/ (LTA + LSA) | Si | Al | Na | $SiO_2$/ $Al_2O_3$ |
|---|---|---|---|---|---|
| Example 5.1 | 1 | 44.19 | 2.09 | 1.22 | 40.61 |
| Example 5.2 | 0.75 | 44.15 | 2.11 | 1.24 | 40.66 |
| Comparative Example 5.3 | 0.5 | 44.3 | 2.11 | 1.01 | 40.34 |
| Comparative Example 5.4 | 0.25 | 44.09 | 2.12 | 1.32 | 39.97 |
| Comparative Example 5.5 | 0 | 44.05 | 2.04 | 1.49 | 41.45 |

TABLE 3.2

Surface Areas of MFI made from Zeolite LTA and LSA (Liquid Sodium Aluminate).

| Examples | LTA/ (LTA + LSA) | SA m$^2$/g | MSA m$^2$/g | uPV cc/g | TPV cc/g |
|---|---|---|---|---|---|
| Example 5.1 | 1 | 317 | 10 | 0.159 | 0.189 |
| Example 5.2 | 0.75 | 324 | 25 | 0.155 | 0.216 |
| Comparative Example 5.3 | 0.5 | 330 | 23 | 0.159 | 0.211 |
| Comparative Example 5.4 | 0.25 | 321 | 17 | 0.157 | 0.198 |
| Comparative Example 5.5 | 0 | 297 | 34 | 0.136 | 0.239 |

Example 6

Procedure for xylene vapor uptake measurement by Thermal Gravimetric Analysis (TGA). A loading of about 25 mg of zeolite sized to 40×60 mesh is placed onto the weighing pan of the instrument. The sample is pretreated at 350° C. for 60 minutes in a flowing $N_2$, and its weight recorded after pretreatment. Thereafter, the sample temperature is lowered to the adsorption temperature of 120° C. The uptake experiment is performed by passing a flow of $N_2$ at 72 ml/min through a para-xylene or ortho-xylene saturator controlled at 18° C., which is then combined with a separate $N_2$ flow set at 127 ml/min, before contacting the sample. The time of adsorption for para-xylene is about 40 to 100 minutes and for ortho-xylene is 200 to 240 minutes. The experiment is performed separately for para-xylene adsorption and for ortho-xylene adsorption. Net weight gain of sample is defined as the difference between 1) sample weight upon reaching adsorption equilibrium (and stable weight) or at the end of adsorption experiment, and 2) the sample weight after pretreatment step. The uptake weight percentage of each xylene isomer is defined as the ratio of net weight gain to the weight after pretreatment, and the ortho-xylene to para-xylene uptake ratio is defined as the ratio of ortho-xylene uptake weight percentage to para-xylene uptake weight percentage. The results are summarized in Tables 4 and 5. The results showed that a higher level of xylenes uptake is achieved when the MFI structure has a lower $SiO_2/Al_2O_3$ ratio, and also MFIs in examples 1-5 with specific synthesis protocol showed a lower equilibrium uptake ratio of ortho-/para-xylene than the comparative examples.

TABLE 4

Uptake Characteristics of Examples and Comparative Examples 1 through 4

| Example | Material Description | $SiO_2/Al_2O_3$ | $SiO_2/B_2O_3$ | pX uptake wt % at equil or 240 min | oX uptake wt % at equil or 240 min | oX to pX uptake ratio |
|---|---|---|---|---|---|---|
| Example 1 | MFI EDA/TPA | 49.4 | 54.2 | 4.926 | 1.45 | 0.29 |
| Comparative 1.1 | MFI TPA | 49.7 | 166.1 | 5.895 | 5.063 | 0.86 |
| Example 1.2 | MFI EDA/TPA | 36 | | | | |
| Comparative 1.2 | MFI-TPA | 40 | | 6.1 | 5.06 | 0.83 |
| Example 2 | MFI EDA/TPA | 99.6 | 32.0 | 4.443 | 1.23 | 0.28 |
| Comparative 2.1 | MFI TPA | 99.1 | 105.0 | 4.555 | 3.631 | 0.80 |
| Comparative 2.2 | Zeolyst MFI-80 | 80 | | 4.463 | 3.814 | 0.85 |
| Example 3 | MFI EDA/TPA | 168.0 | 43.5 | 3.27 | 1.16 | 0.35 |
| Comparative 3.1 | MFI TPA | 160.7 | 70.8 | 3.75 | 2.728 | 0.73 |
| Comparative 3.2 | MFI-TPA | 190 | | 3.012 | 1.735 | 0.58 |
| Example 3.3 | MFI EDA/TPA | 221 | 42.7 | 3.14 | 0.90 | 0.29 |
| Comparative 3.4 | MFI TPA | 186 | 70.2 | 3.68 | 2.52 | 0.68 |
| Example 3.5 | MFI EDA/TPA | 400 | 40.1 | 2.51 | 0.95 | 0.38 |
| Comparative 3.6 | MFI TPA | 441 | 63.1 | 3.17 | 1.49 | 0.47 |
| Example 3.7 | MFI EDA/TPA | 591 | 37.3 | 2.42 | 0.40 | 0.17 |
| Comparative 3.8 | MFI TPA | 500 | | 2.50 | 1.29 | 0.52 |
| Comparative Example 4 | U.S. Pat. No. 4,257,885 | 44 | | 6.339 | 3.064 | 0.48 |

TABLE 5

Uptake Characteristics of Examples and Comparative Examples 5

| Examples | LTA/ (LTA + LSA) | pX uptake wt % at equil | oX uptake wt % at equil or 240 min | oX to pX uptake ratio |
|---|---|---|---|---|
| Example 5.1 | 1 | 6.059 | 1.83 | 0.30 |
| Example 5.2 | 0.75 | 6.266 | 3.112 | 0.50 |
| Comparative Example 5.3 | 0.5 | 5.812 | 4.665 | 0.80 |
| Comparative Example 5.4 | 0.25 | 5.642 | 4.988 | 0.88 |
| Comparative Example 5.5 | 0 | 5.195 | 4.53 | 0.87 |

Example 7

Procedure for normal heptane (nC7) cracking tests. A catalyst loading of 250 mg sized to 40×60 mesh is first pretreated at 625° C. in a flowing $N_2$ for 60 minutes. The catalytic performance is evaluated at one atmosphere pressure and at variable temperatures of 483, 533, 608 (sequentially) and then return to 483° C. with a constant $N_2$ flow at 125 ml/minute passing through normal heptane saturator controlled at 0° C. GC method is set up to capture light paraffin and olefin, benzene, toluene, xylene isomers/ethylbenzene and $C_5$-$C_9$ non-aromatics.

MFIs prepared as per Examples 1-3 and Comparative Examples 1-4 are ion-exchanged as previously described to be in $NH_4^+/H^+$ (c) form prior to catalytic tests. In separate nC7 cracking experiments, MFIs are also hydrothermally treated at 650 and 760° C. at 40% steam over a period of 12 hours, respectively, prior to gauging catalytic performance.

As shown in FIGS. 2 to 13, At $SiO_2/Al_2O_3$ ratios of 40-50, EDA-MFI exhibits significantly lower activities across the entire range of temperatures. Unlike TPA-MFI, its activities exhibit near zero or negative responses to increased temperatures. Furthermore, when returning the initial condition, its activity drops to zero, suggesting severe deactivation. As $SiO_2/Al_2O_3$ ratios increase from 50, to 100 and then 160-170, the activity and light olefin yield gaps first narrows and then reverses. The activity and light olefin yield responses to temperatures of EDA-MFI turns from negative, linear and then exponential. The same transformation of performance ranking with respect to $SiO_2/Al_2O_3$ is also observed, when MFIs are subject to hydrothermal treatment, designed to mimic the hydrothermal environments the zeolite would be exposed to process and regeneration conditions. The higher productivity of light olefin and improved response to temperatures, with increased $SiO_2/Al_2O_3$ ratios and/or hydrothermal treatment, is illustrated in FIGS. 2-13, suggesting that, without being bound by theory, active sites in the tortuous channels have higher intrinsic activity and/or better hydrothermal stability.

To further illustrate the utility of active sites located in the constraint environment, the paraffin cracking test is modified to obtained performance at earlier times on stream comparable to the contacts representative of processes such as fluidized beds, riser etc. The modified paraffin cracking test involves the same 625° C., 1-hour $N_2$ pretreatment procedure and measures performances at temperatures of 500, 550, 625, and 500° C. sequentially (483, 533, 608 and 483° C. reactor temperatures). Normal heptane feed is still introduced via flowing $N_2$ at 125 ml/minute through a saturator of liquid normal heptane controlled at 0° C., but at each temperature, the catalyst is only exposed to paraffin vapor feed for 5 minutes before GC sampling of product and flow is switched to pure $N_2$ immediately afterwards, and catalyst stays in pure $N_2$ flow at 125 ml/min during transition to the next condition. The contact in the modified paraffin cracking test corresponds to a catalyst to feed ratios on a weight basis from about 1 to about 10.

Figure 11:
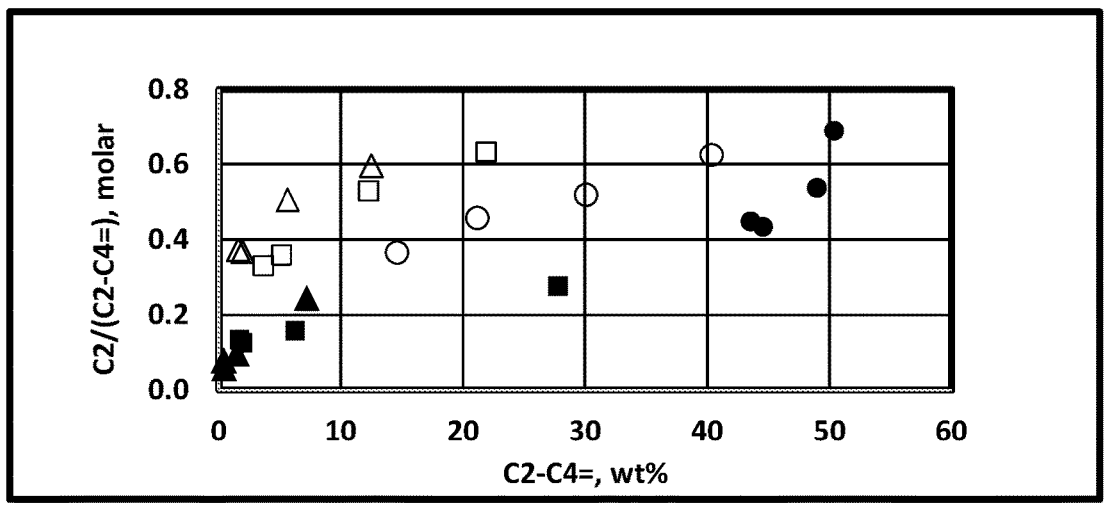
In FIG. 11, open circles, squares, and triangles are achieved over the MFI of Example 1 in H+ form, after steaming at 650° C., and after steaming at 760° C. respectively. Filled circles, squares and triangles are achieved over the MFI of Comparative Examples 1.1 or 1.2 in H+ form, after steaming at 650° C., and after steaming at 760° C. respectively.
Figure 12:
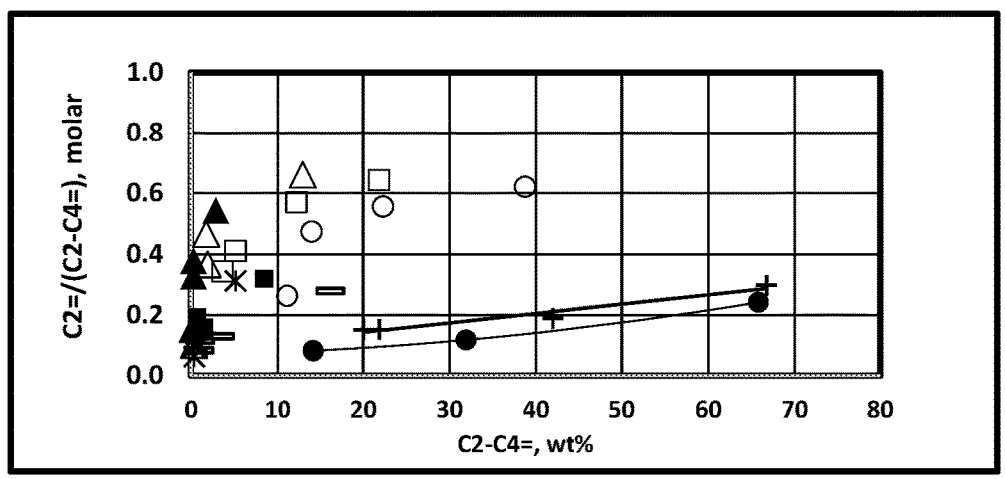
In FIG. 12, open circles, squares, and triangles are achieved over the MFI of Example 2 in H+ form, after steaming at 650° C., and after steaming at 760° C. respectively. Filled circles, squares and triangles are achieved over the MFI of Comparative Example 2.1 in H+ form, after steaming at 650° C., and after steaming at 760° C. respectively. Plus, dash, and star symbols are achieved over the MFI of Comparative Example 2.2 in H+ form, after steaming at 650° C., and after steaming at 760° C. respectively.
Figure 13:
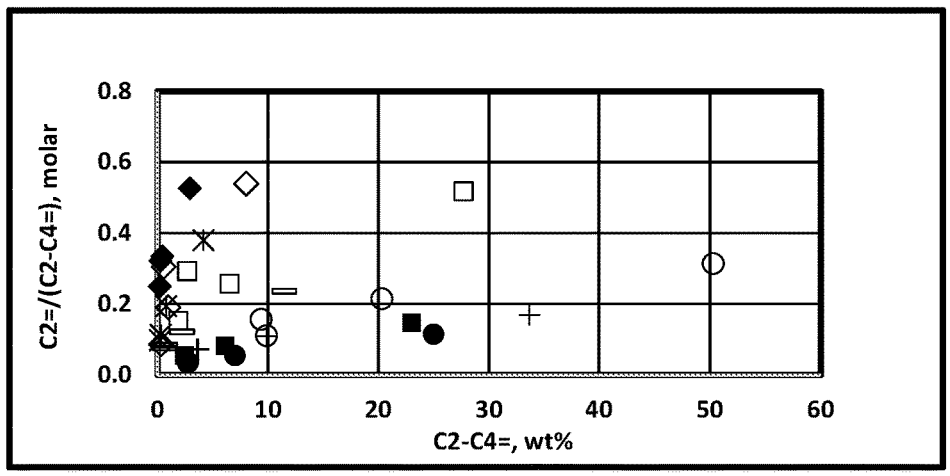
In FIG. 13, open circles, squares, and triangles are achieved over the MFI of Example 3 in H+ form, after steaming at 650° C., and after steaming at 760° C. respectively. Filled circles, squares and triangles are achieved over the MFI of Comparative Example 3.1 in H+ form, after steaming at 650° C., and after steaming at 760° C. respectively. Plus, dash, and star symbols are achieved over the MFI of Comparative Example 3.2 in H+ form, after steaming at 650° C., and after steaming at 760° C. respectively.

As shown in FIGS. 2-13, paraffin cracking to light olefin (C2-C4) are becoming more favorable for MFIs containing active sites in constrained environments, with increased $SiO_2/Al_2O_3$ ratios and/or hydrothermal treatment, and especially pronounced for converting paraffin to lighter olefin (C2-C3) as shown in FIGS. 2-13. It is further observed that the active sites located in the constraint environment favorably produce ethylene as shown in FIGS. 11-13, the levels of which are below thermodynamically allowable levels due to high energetic barriers for olefin interconversions from higher olefins to ethylene. Conceivably, for catalytic processes such as oxygenates to light olefin, hydrocarbon cracking to light olefin, olefin inter-conversion to lighter olefins, it is useful to deploy MFI zeolite containing active sites located in the constraint environment to co-produce ethylene and propylene, and especially to co-produce ethylene and propylene at high proportions of ethylene. Conversely, one would limit the active sites located in the constraint environment to minimize ethylene production if the process objective is to maximize propylene production or propylene/butylene co-production.

Figure 14:
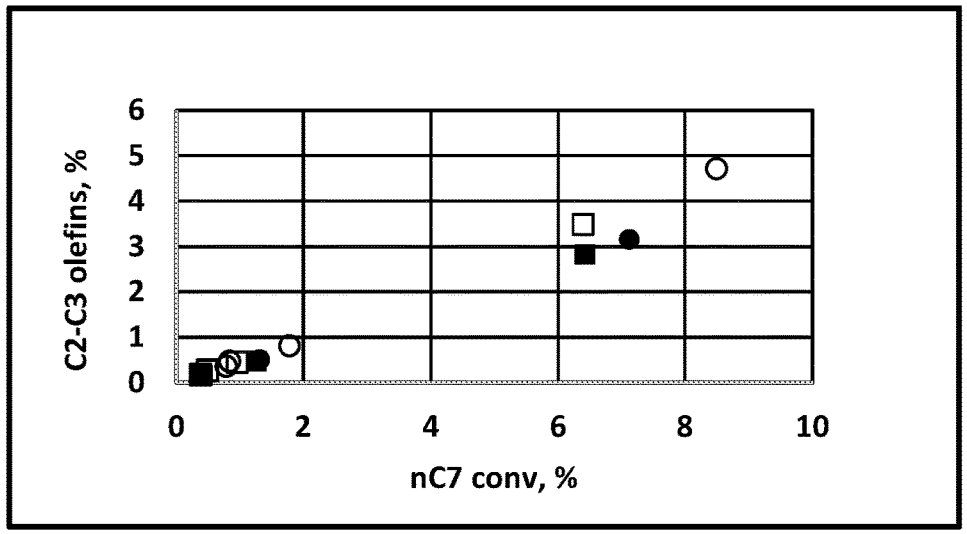
FIG. 14 shows a plot of the moles of ethylene and propylene to heptane conversion achieved during the modified paraffin cracking test of the present disclosure.
Figure 15:
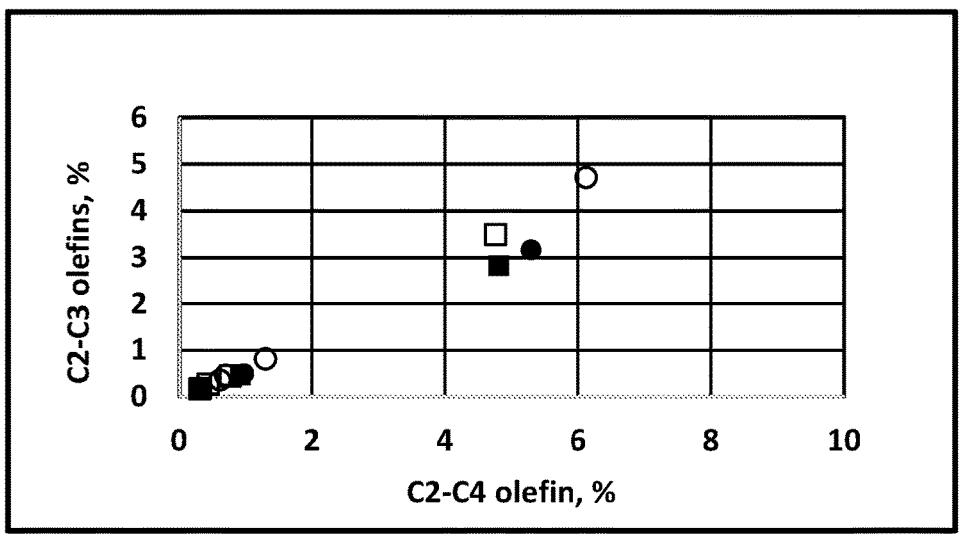
FIG. 15 shows a plot of the moles of ethylene and propylene to total moles of ethylene, propylene, and butene as a function of the weight percent of ethylene, propylene, and butene achieved during the modified paraffin cracking test of the present disclosure.
Figure 16:
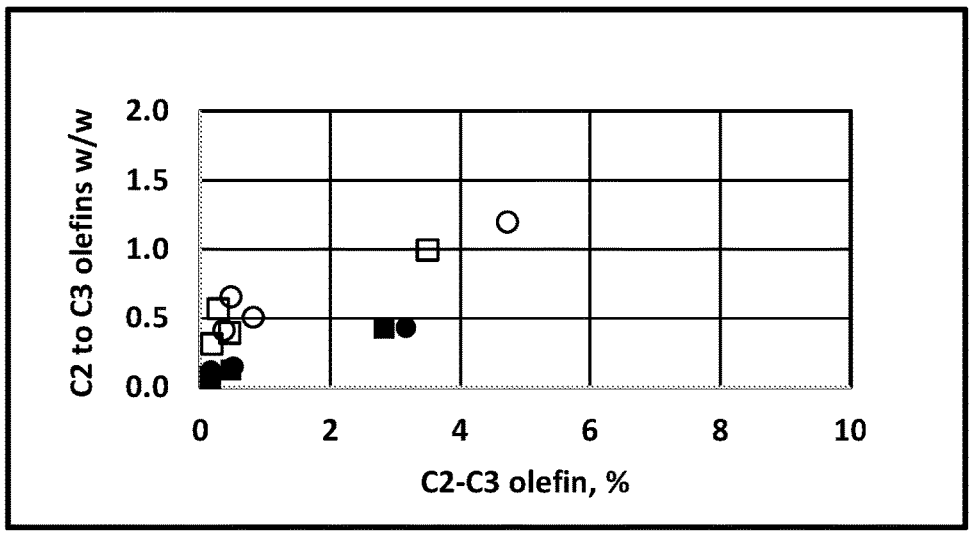
FIG. 16 shows a plot of the ratio of ethylene and propylene to total moles of ethylene, propylene, and butene as a function of the weight percent of ethylene, propylene, and butene achieved during the modified paraffin cracking test of the present disclosure. Filled squares in FIGS. 14, 15, and 16 are from the material of Comparative Example 1.2. Filled circles in FIGS. 14, 15, and 16 are from the material of Comparative Example 1.1. Open squares in FIGS. 14, 15, and 16 are from the material of Example 1.2. Open circles in FIGS. 14, 15, and 16 are from the material of Example 1.
Figure 17:
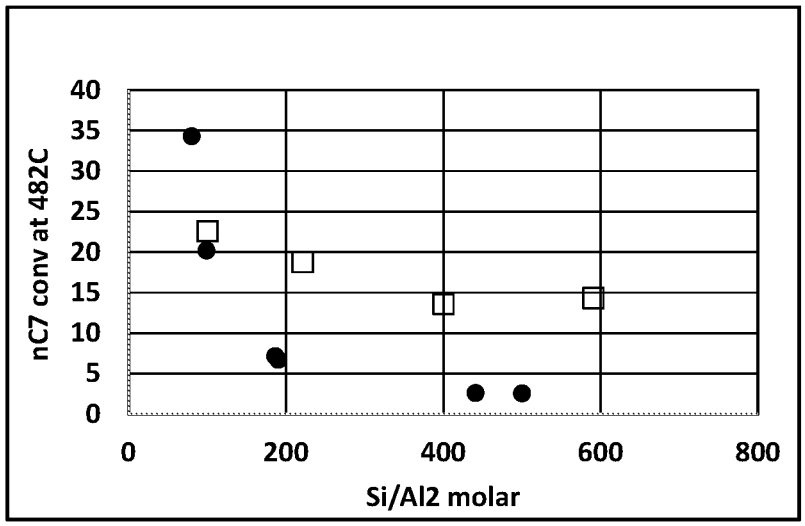
FIG. 17 shows a plot of heptane conversion against silica to alumina ratio.
Figure 18:
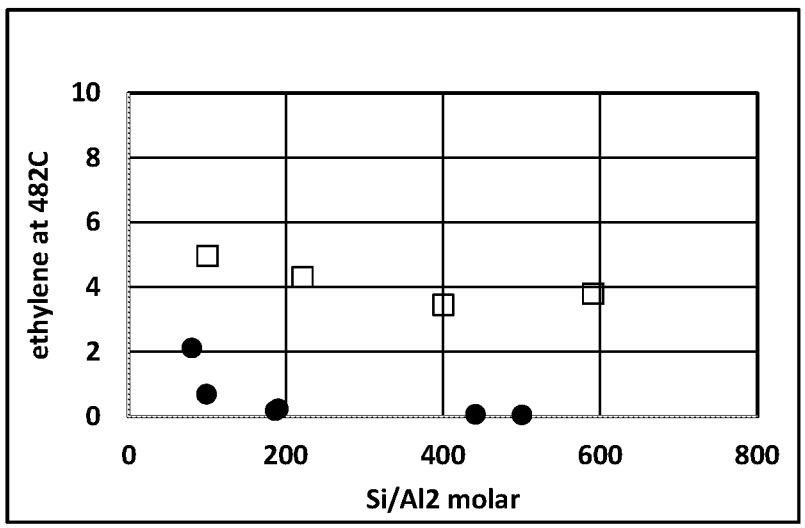
FIG. 18 shows a plot of ethylene weight percent versus silica to alumina ratio.
Figure 19:
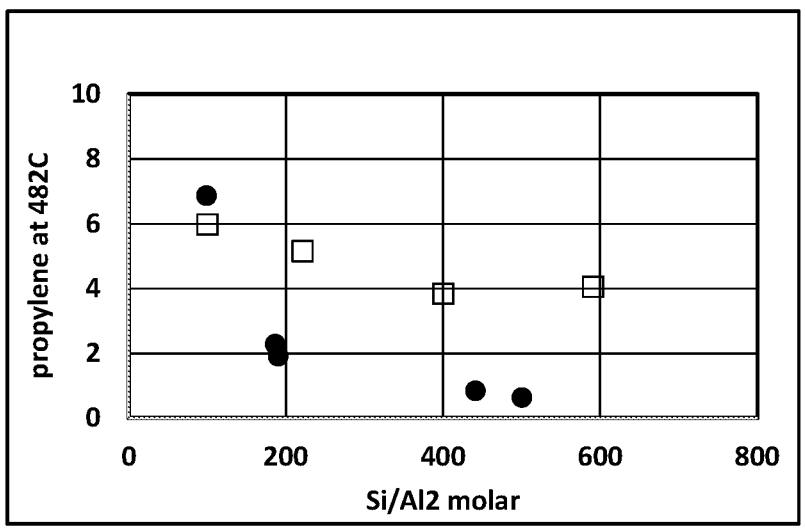
FIG. 19 shows a plot of propylene weight percent versus silica to alumina ratio.
Figure 20:
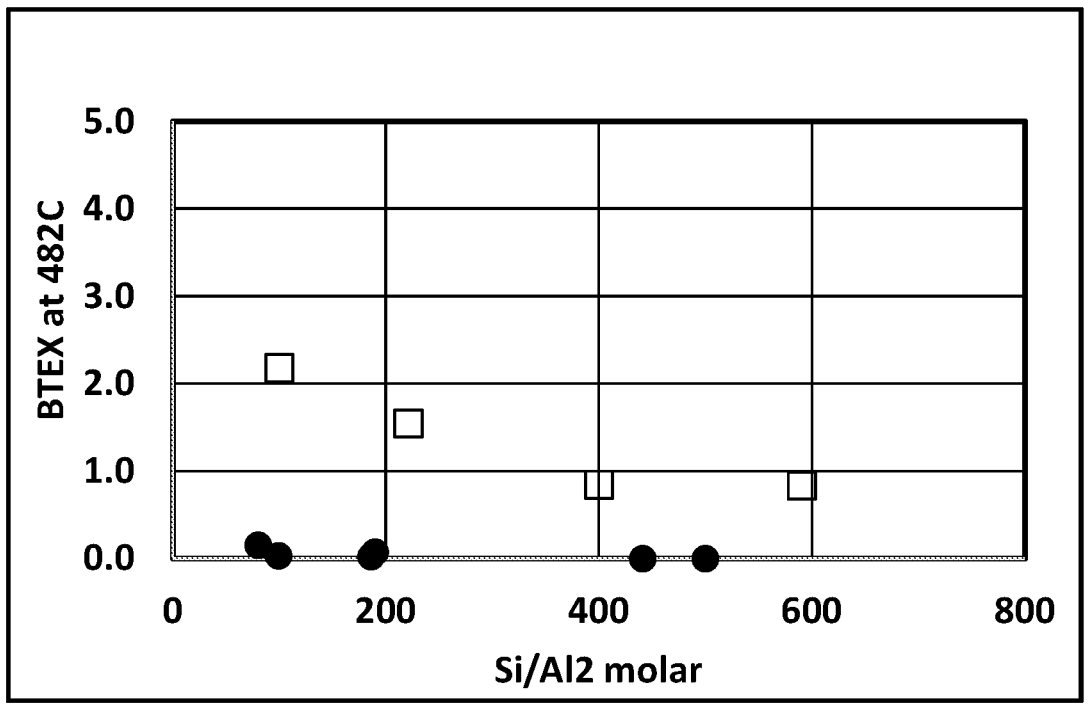
FIG. 20 shows a plot of BTEX (benzene, toluene, ethylbenzene and xylene combined) against silica to alumina ratio.
Figure 21:
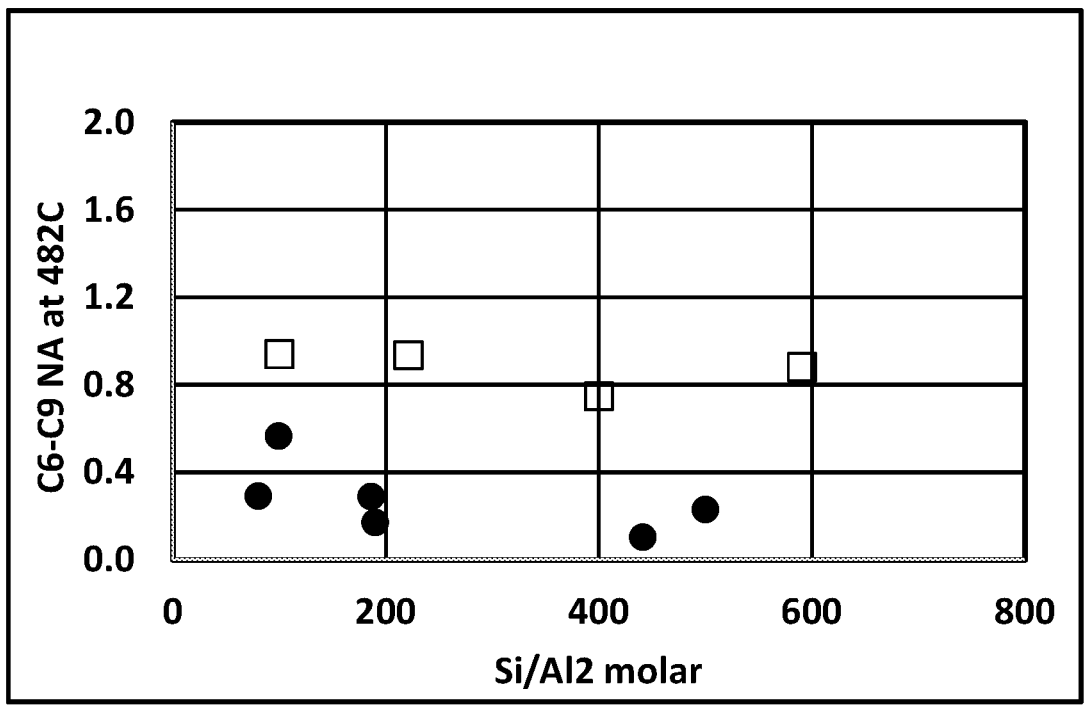
FIG. 21 shows a plot of C6-C9 NA (non-aromatics hydrocarbons ranging from 6 to 9 carbon numbers) versus silica to alumina ratio. Open squares in FIGS. 17-21 are from Examples 3 of the instant invention. Closed circles in FIGS. 17-21 are from Comparative Examples 3.
Figure 22:
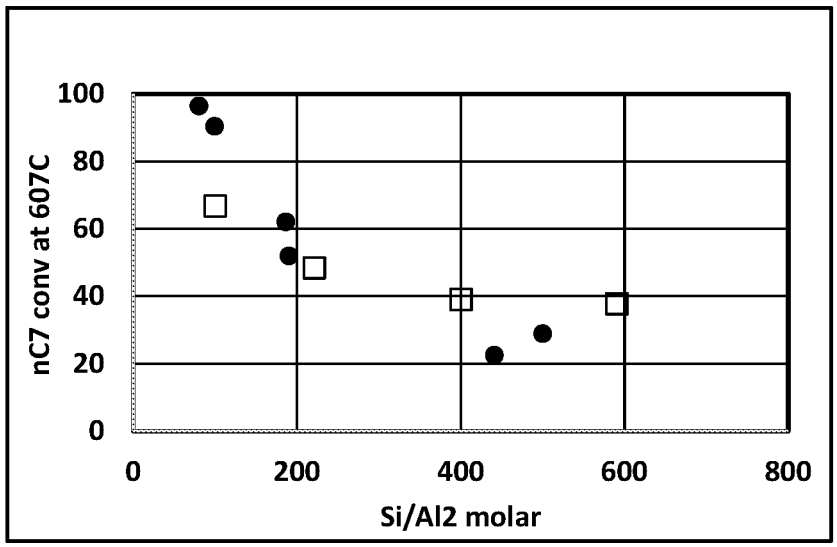
FIG. 22 shows a plot of heptane conversion against silica to alumina ratio.
Figure 23:
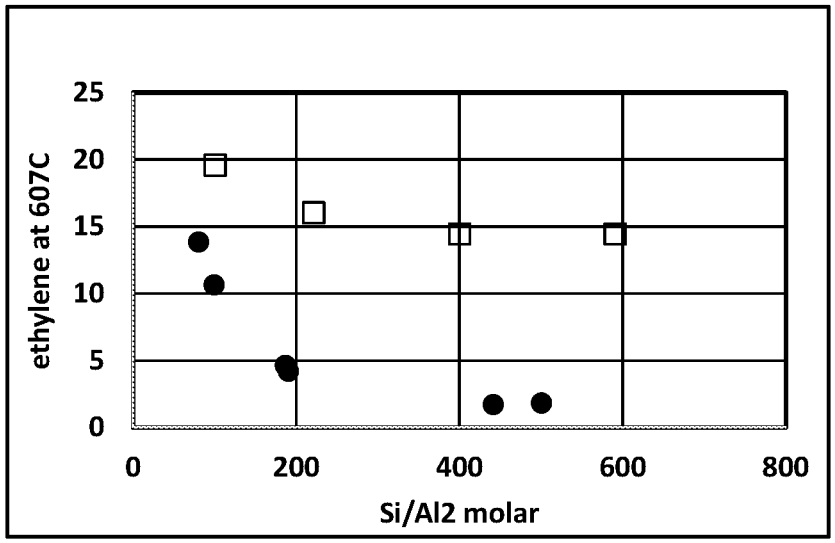
FIG. 23 shows a plot of ethylene weight percent versus silica to alumina ratio.
Figure 24:
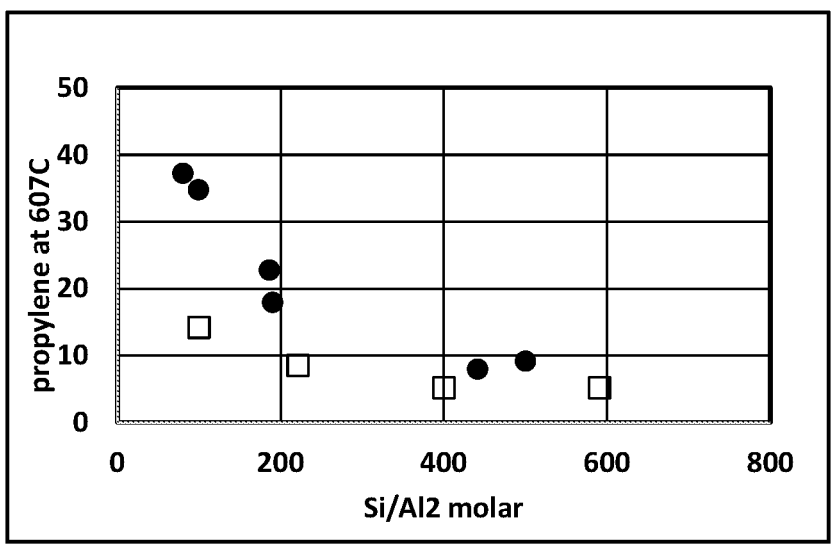
FIG. 24 shows a plot of propylene weight percent versus silica to alumina ratio.
Figure 25:
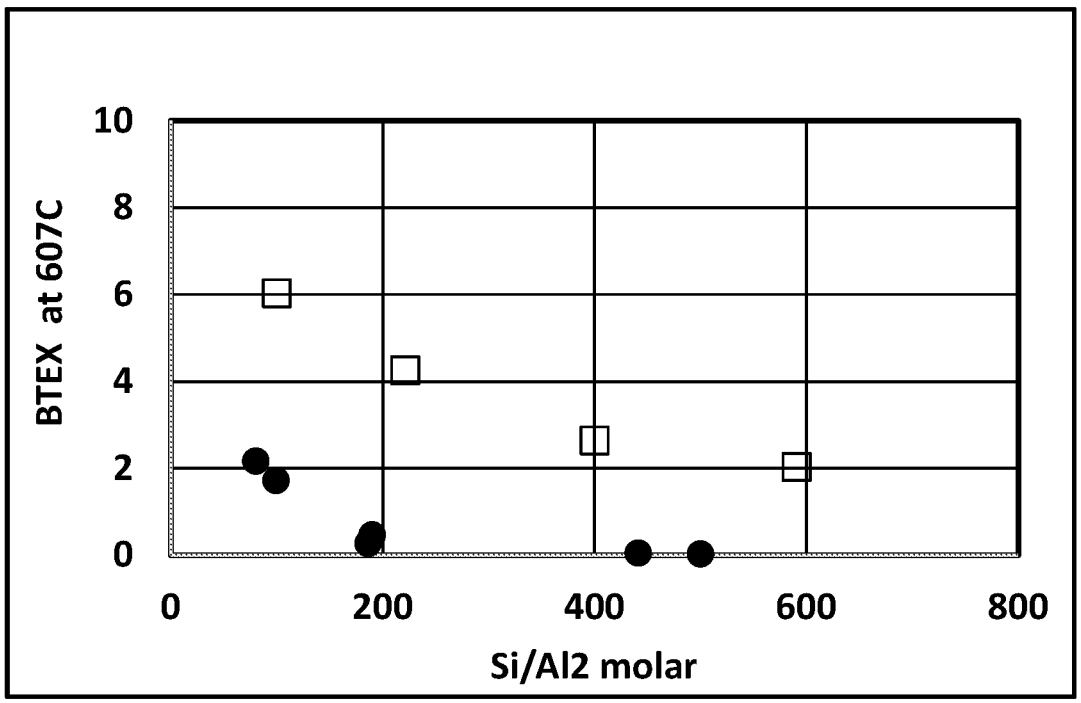
FIG. 25 shows a plot of BTEX against silica to alumina ratio.
Figure 26:
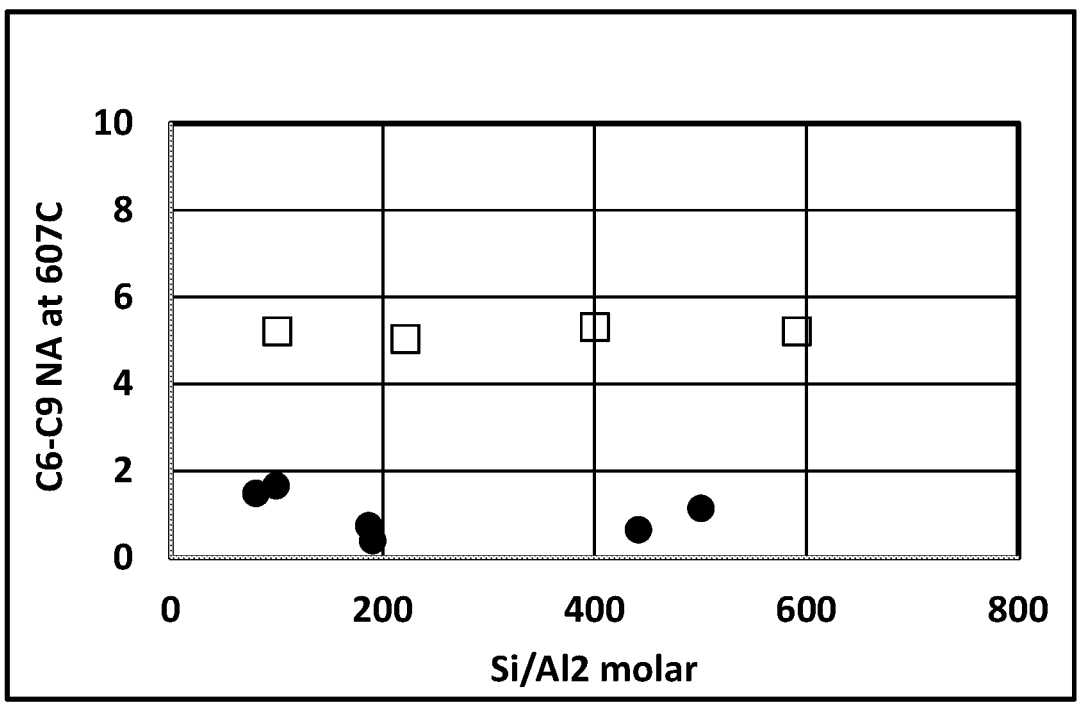
FIG. 26 shows a plot of C6-C9 NA versus silica to alumina ratio. Open squares in FIGS. 22-26 are from Examples 3 of the instant invention. Closed circles in FIGS. 22-26 are from Comparative Examples 3.
Figure 27:
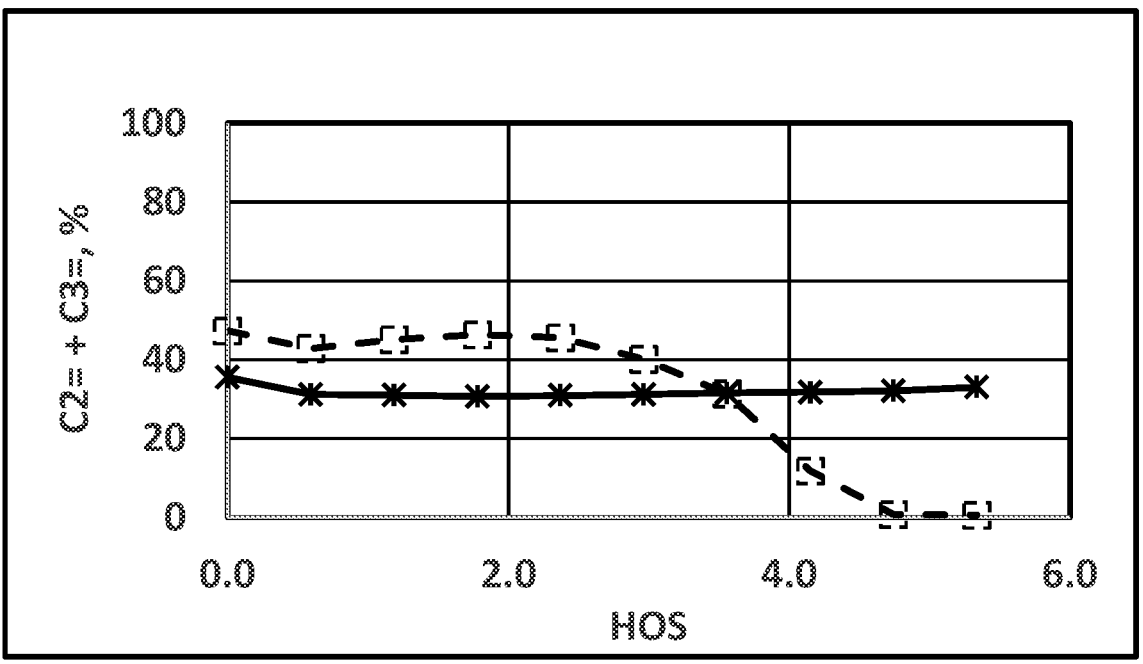
FIG. 27 is the H+ form of the calcined materials, FIG. 28 from materials steamed at 650° C.
Figure 28:
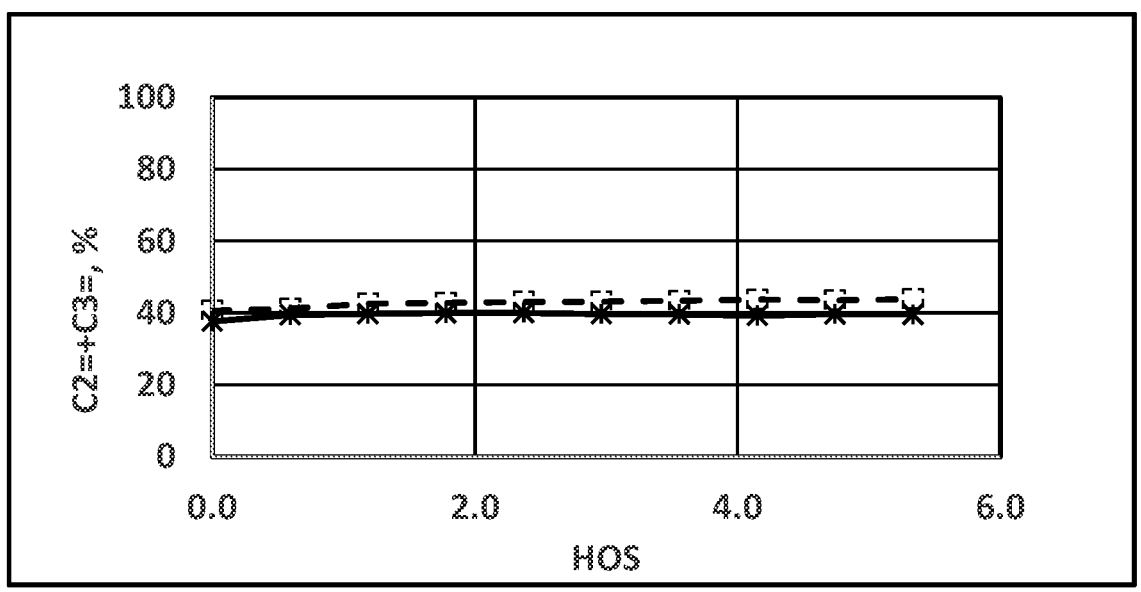
Figure 29:
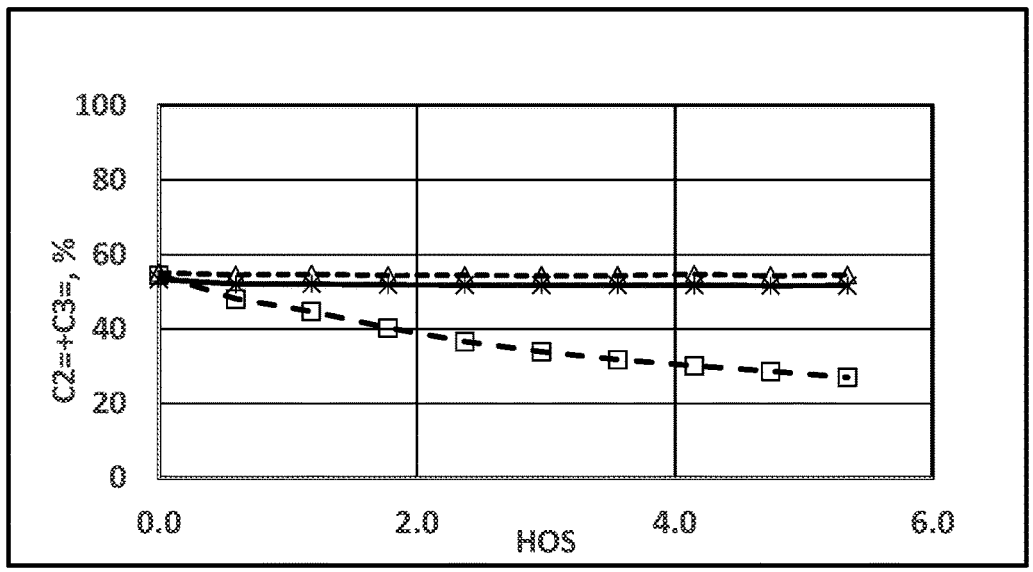
FIG. 29 is the H+ form of the materials, FIG. 30 from materials steamed at 650° C.
Figure 30:
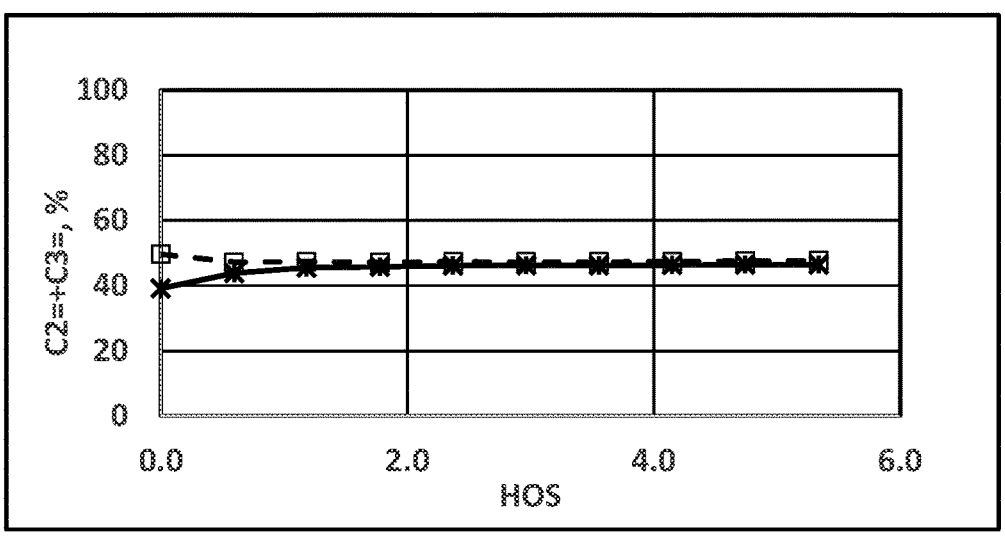
Figure 31:
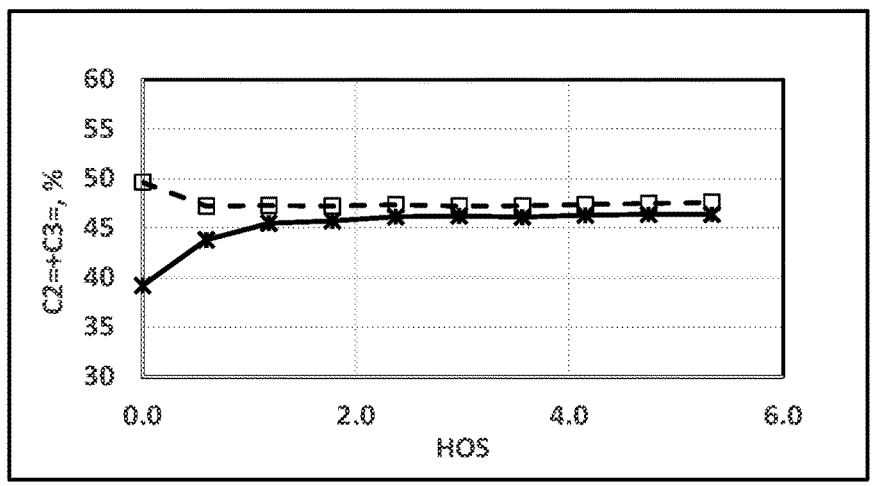
FIG. 31 after steaming at 760° C.
Figure 32:
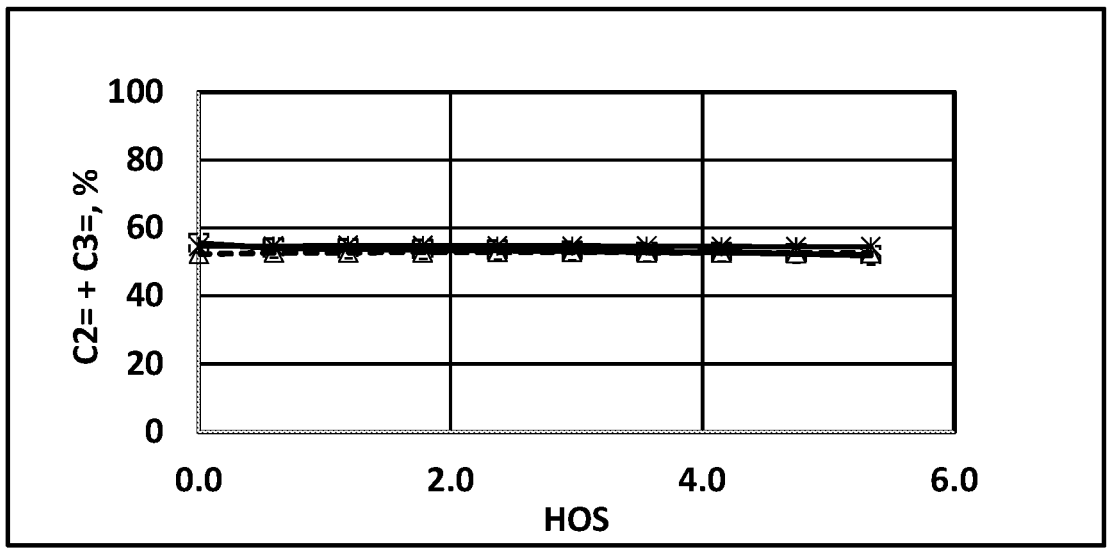
FIG. 32 is the H+ form of the materials, FIG. 33 from materials steamed at 650° C.
Figure 33:
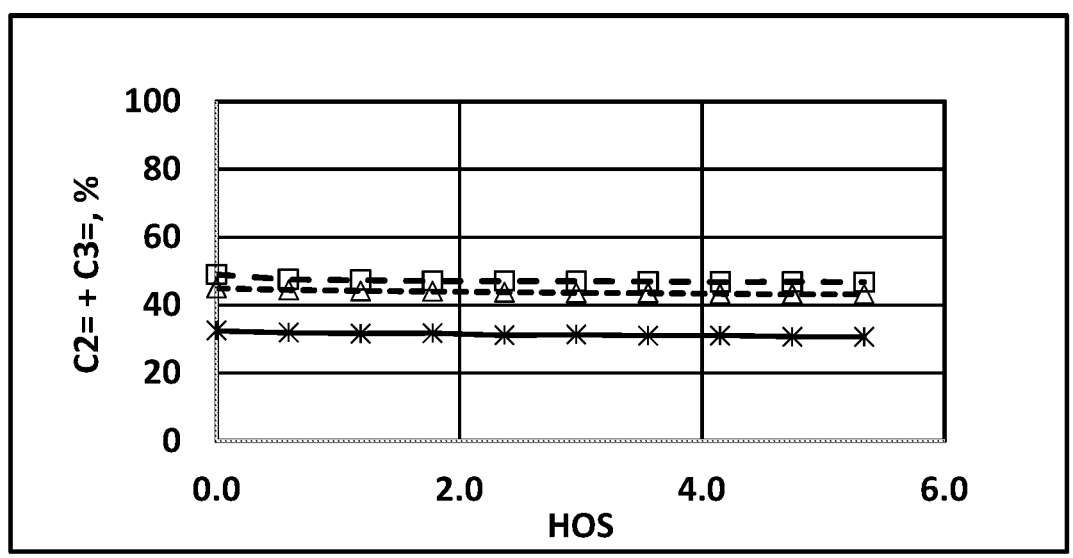
Figure 34:
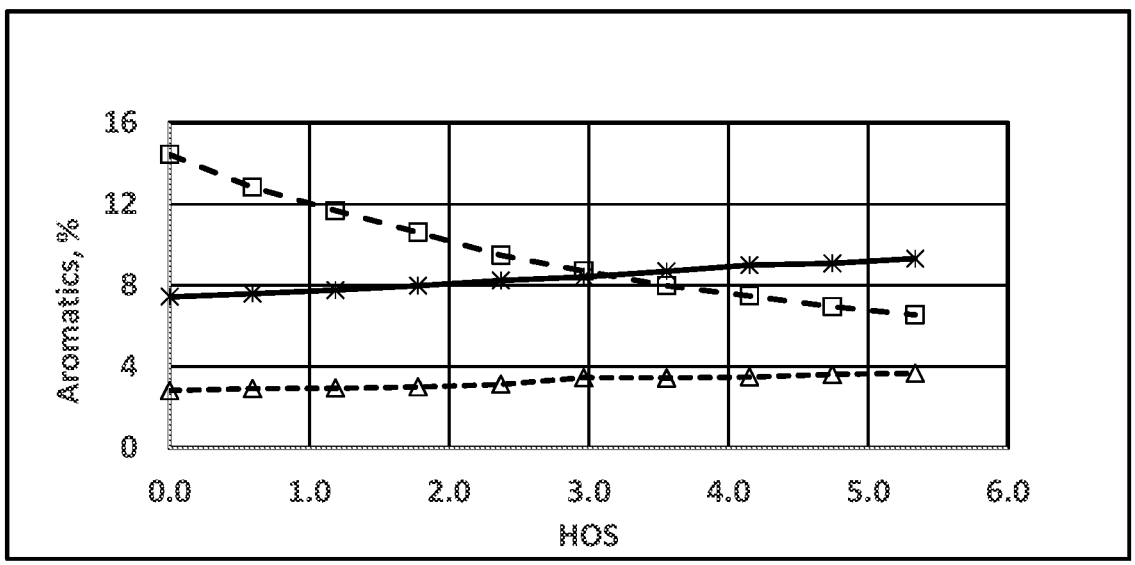
FIG. 34 is the H+ form of the materials, FIG. 35 from materials steamed at 650° C.
Figure 35:
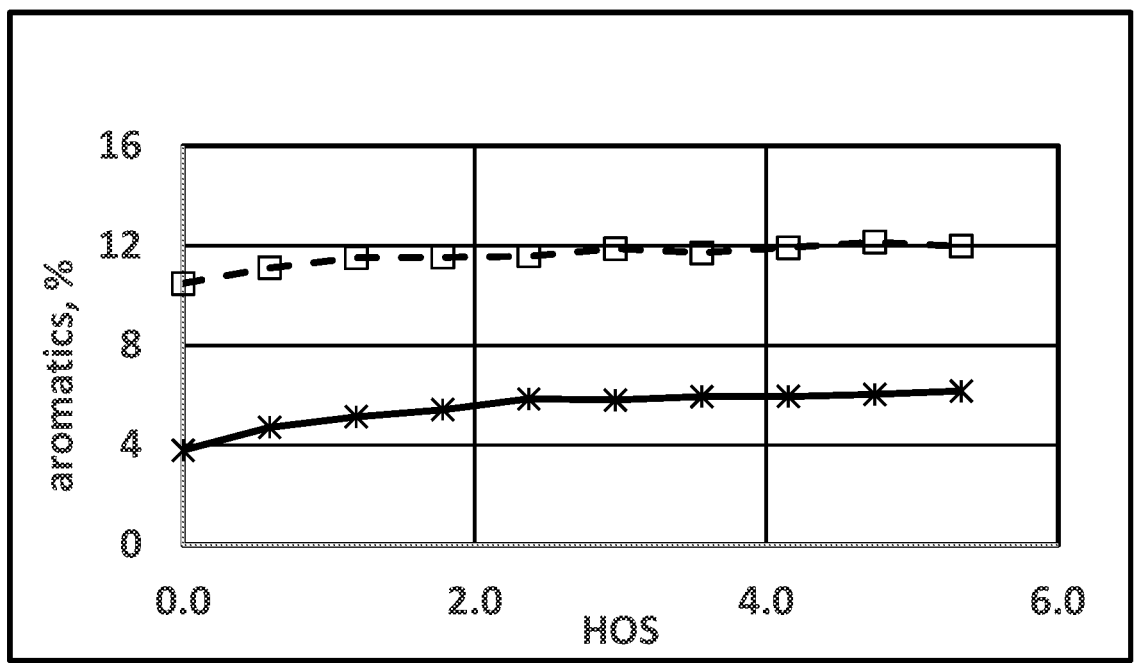
Figure 36:
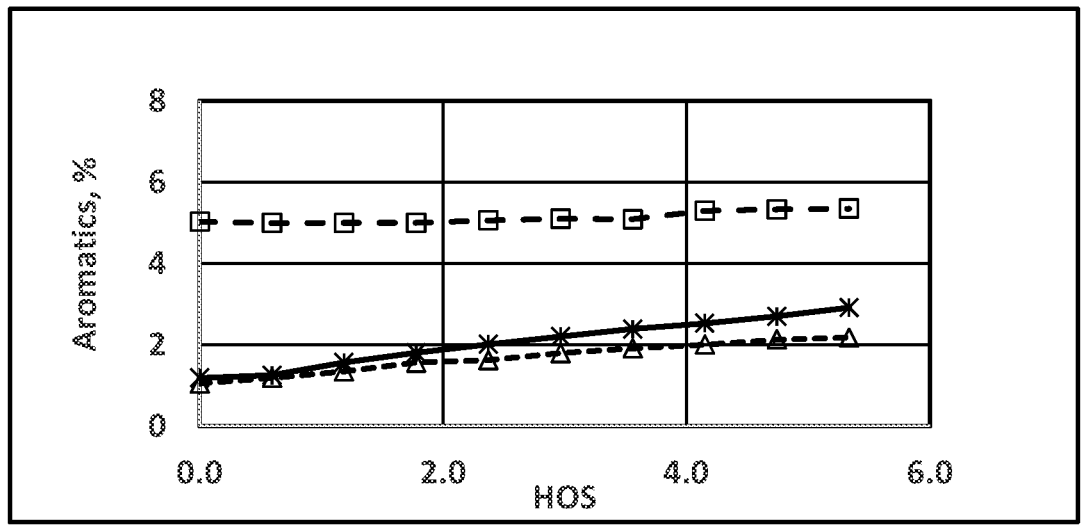
FIG. 36 is the H+ form of the materials, FIG. 37 from materials steamed at 650° C.
Figure 37:
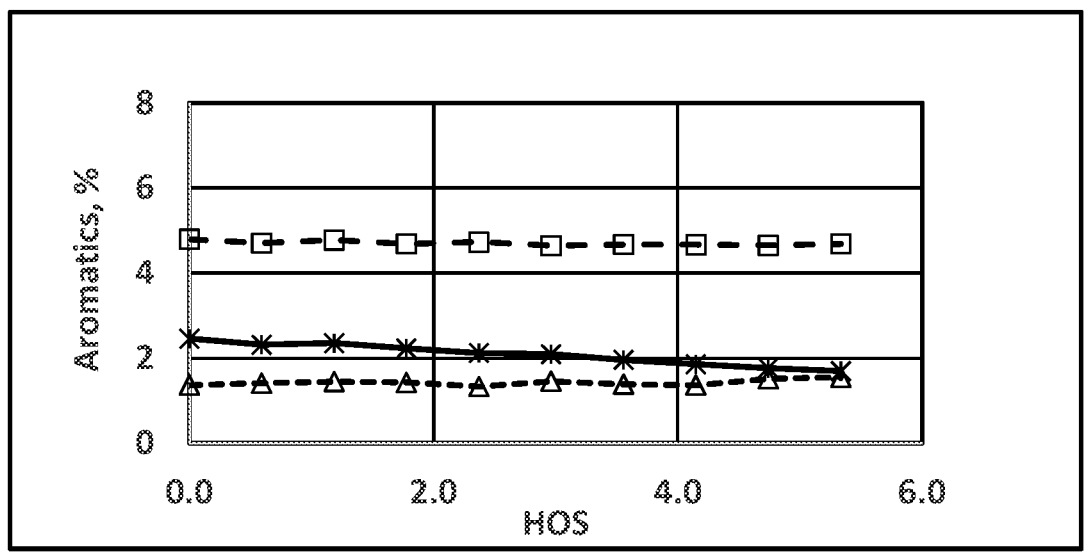
Figure 38:
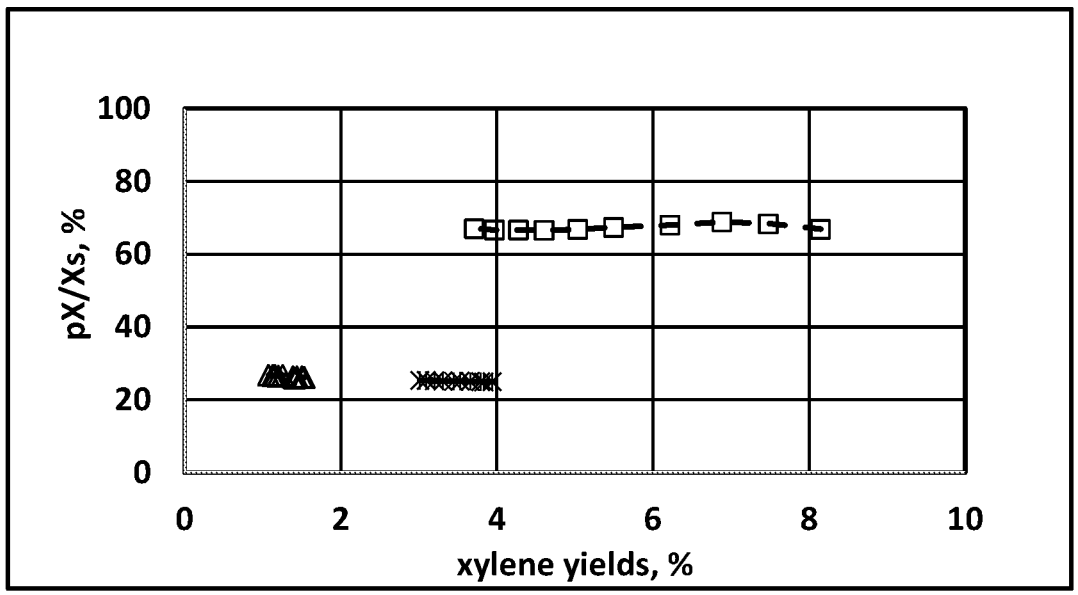
FIG. 38 is the H+ form of the materials, FIG. 39 from materials steamed at 650° C.
Figure 39:
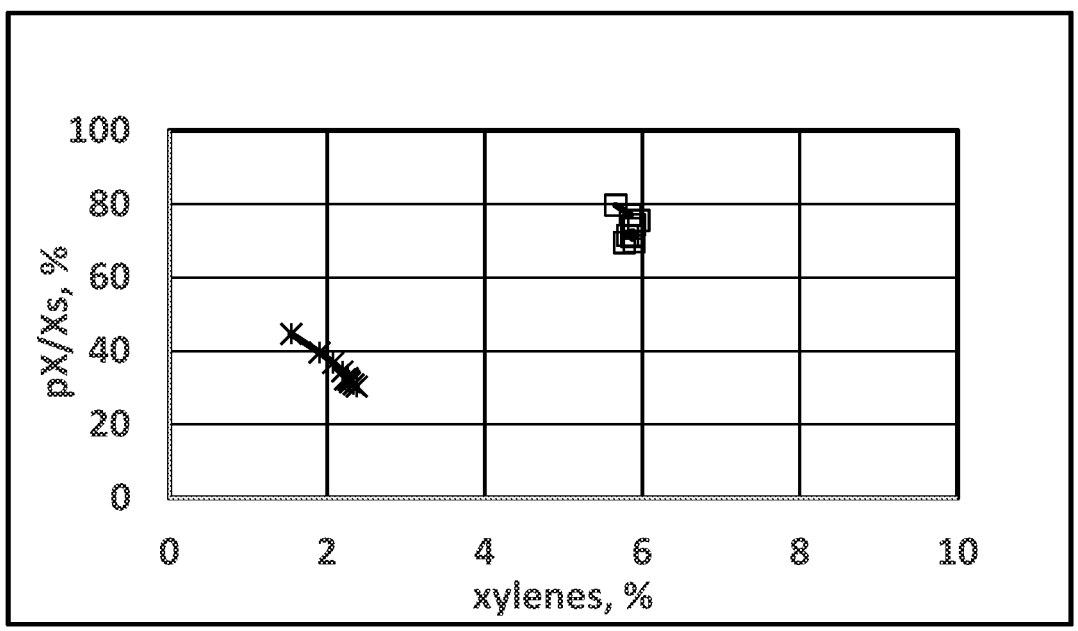
Figure 40:
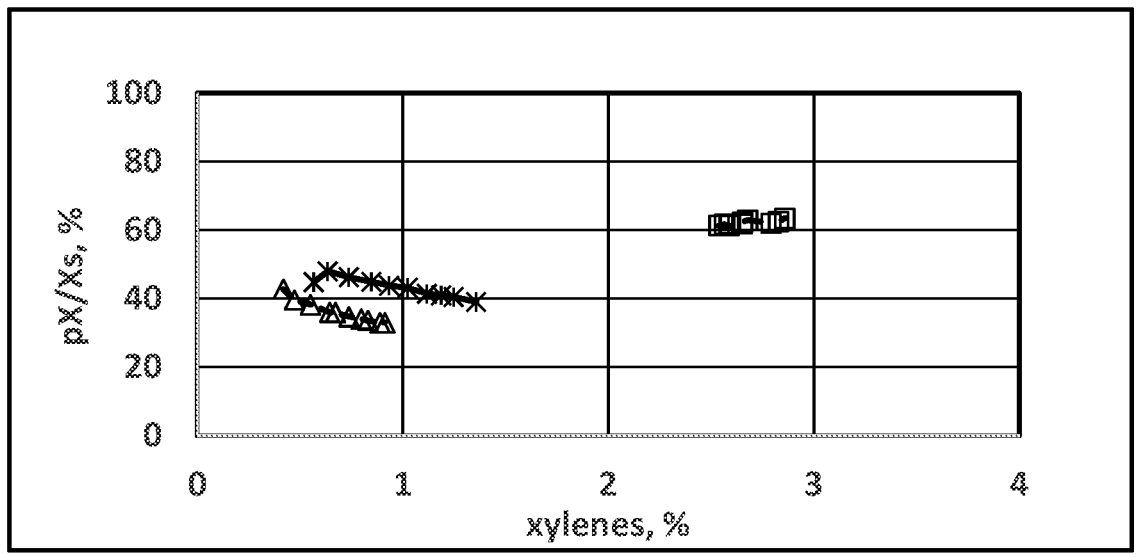
FIG. 40 is the H+ form of the materials, FIG. 41 from materials steamed at 650° C.
Figure 41:
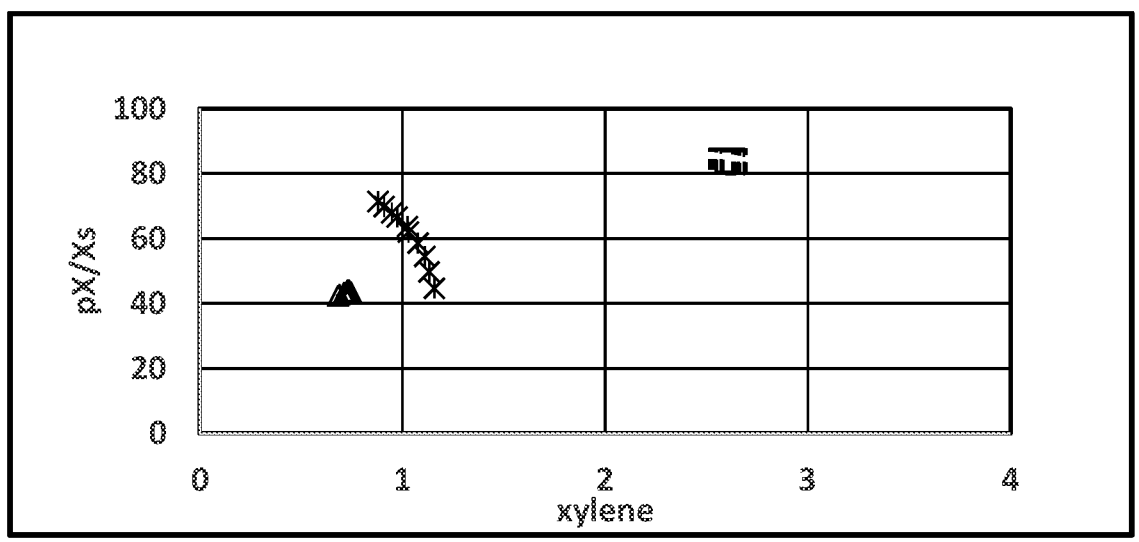

To further assess the hydrothermal severity impact on catalyst performance, such as that occurring in fluid catalytic cracking processes, zeolites of Example 1 were subjected to 100% steam at 796° C. for 16 hours. As shown in FIGS. 14-16, zeolite of Examples 1 of the instant invention exhibited higher ethylene and propylene percentages and higher ethylene and propylene percentages at given heptane conversions than those of Comparative Examples 1. Furthermore, ethylene to propylene ratios (w/w) for materials of the instant invention are approximately double those of Comparative Examples 1 at ethylene plus propylene weight percentages (FIG. 16).

It is noted that TPA-MFI (Comparative Examples 5) is directed toward propylene and butylene production. It's activity to produce C2-C4 olefin was adversely impacted, when exposed to hydrothermal exposure incurred during conversion and regeneration unit operations in olefin producing processes. Furthermore, its activity to produce light olefins is greatly impacted by $Si/Al_2$ ratio as shown in FIGS. 17-26. With increasing $Si/Al_2$ ratios from about 80 to about 600, the activities in producing ethylene and propylene are adversely impacted, requiring significantly higher temperature to trigger the light olefin production.

On the other hand, EDA/TPA MFI materials of the instant invention are geared toward ethylene and propylene production. They have distinctly higher activity in producing ethylene and propylene, are relatively insensitive to $Si/Al_2$ of about 100 to about 600 as shown in FIGS. 17-19 and 22-24. We conceive that ethylene and propylene may be maximized by combining EDA/TPA-MFI materials of the instant invention with TPA-MFI of Comparative Examples. Without being bound by theory, it appears an increased amount of ethylene and propylene is attained by converting butylene and higher olefin to ethylene and propylene on active sites pertaining to EDA/TPA MFI as shown in Tables 6 to attain ethylene to propylene ratios greater than about 0.4 ratio on a weight basis. Preferably, greater than 20% and less than about 95% of TPA-MFI of $Si/Al_2$ less than about 2500 is employed with the balance being EDA/TPA-MFI of $Si/Al_2$ ratios greater than about 100. Most preferably, greater than 40% and less than about 90% about of TPA-MFI of $Si/Al_2$ less than about 200 is employed with the balance being EDA/TPA-MFI of $Si/Al_2$ ratios greater than 200.

TABLE 6.1

Modified n-Heptane Cracking Test of a Physical Mixture of EDA- and TPA-MFI

| % EDA | C7 Conv | | | C2 to C4 olefins selectivity | | |
|---|---|---|---|---|---|---|
| MFI/Temp ° C. | 482.96 | 532.95 | 607.99 | 482.96 | 532.95 | 607.99 |
| 0 | 8.06 | 20.32 | 63.18 | 67.46 | 67.10 | 71.78 |
| 5 | 9.01 | 21.74 | 59.53 | 69.10 | 68.81 | 70.33 |
| 10 | 9.93 | 21.74 | 54.85 | 70.86 | 69.22 | 69.17 |
| 25 | 11.85 | 23.48 | 55.11 | 72.49 | 69.77 | 66.97 |
| 50 | 12.23 | 22.81 | 48.51 | 72.97 | 68.57 | 63.36 |
| 75 | 15.44 | 26.45 | 49.28 | 72.34 | 67.85 | 60.49 |
| 100 | 16.41 | 25.93 | 38.47 | 70.06 | 65.59 | 59.12 |

TABLE 6.2

Modified n-Heptane Cracking Test of a Physical Mixture of EDA- and TPA-MFI

| % EDA | C2 = plus C3 = selectivity | | | C2 = to C3 = w/w ratios | | |
|---|---|---|---|---|---|---|
| MFI/Temp ° C. | 482.96 | 532.95 | 607.99 | 482.96 | 532.95 | 607.99 |
| 0 | 34.39 | 36.78 | 44.26 | 0.08 | 0.12 | 0.22 |
| 5 | 39.56 | 43.02 | 48.88 | 0.24 | 0.34 | 0.49 |
| 10 | 41.78 | 44.87 | 50.13 | 0.28 | 0.41 | 0.61 |
| 25 | 45.83 | 49.30 | 52.76 | 0.40 | 0.60 | 0.93 |
| 50 | 49.78 | 52.46 | 53.04 | 0.56 | 0.85 | 1.36 |
| 75 | 52.95 | 55.89 | 53.45 | 0.73 | 1.16 | 1.95 |
| 100 | 54.86 | 56.96 | 53.84 | 0.92 | 1.49 | 2.55 |

When applying the modified paraffin cracking test to LTA-MFI of the Example 5 series, it was noted that at elevated temperatures of about 600° C., materials of the instant invention (LTA-derived MFIs) in Examples 5.1, 5.2 exhibited higher $C_2$-$C_4$ olefin and lower methane, lower $C_6$-$C_9$ non-aromatics and lower aromatics than materials of Comparative Examples 5.3, 5.4, 5.5, see Table 7. The constraint active sites derived by using zeolite LTA as the aluminum source in the syntheses appear to lower the cracking activities at lower temperatures consistent with lower ortho- to para-xylene uptake ratios. However, at elevated temperatures of around 600° C., cracking to olefin activities have caught up, while $H_2$ transfer reactions for light paraffin and aromatics remained suppressed.

TABLE 7

Modified n-Heptane Cracking Test of LTA-MFIs

| | Example 5.1 | | | Comparative Ex. 5.3 | | | Comparative Ex. 5.4 | | | Comparative Ex. 5.5 | | |
|---|---|---|---|---|---|---|---|---|---|---|---|---|
| Temperature ° C. | 482 | 532 | 607 | 482 | 532 | 607 | 482 | 532 | 607 | 482 | 532 | 607 |
| C1 | 2.4 | 3.8 | 6.0 | 4.4 | 6.7 | 8.0 | 4.6 | 6.5 | 7.9 | 4.0 | 5.6 | 7.1 |
| C2 = | 9.2 | 14.1 | 24.9 | 14.0 | 20.3 | 29.2 | 13.9 | 20.2 | 29.3 | 12.4 | 18.1 | 28.1 |
| C3 = | 20.4 | 27.7 | 29.1 | 22.1 | 25.0 | 21.0 | 22.4 | 25.0 | 20.3 | 22.6 | 26.9 | 23.6 |
| C4 = | 9.5 | 11.0 | 6.1 | 8.6 | 6.6 | 2.3 | 8.9 | 6.8 | 2.2 | 9.6 | 8.7 | 3.1 |
| C2-C3 = | 29.5 | 41.8 | 53.9 | 36.1 | 45.3 | 50.2 | 36.3 | 45.1 | 49.6 | 35.0 | 45.0 | 51.7 |
| C2-C4 = | 39.1 | 52.8 | 60.0 | 44.7 | 51.9 | 52.5 | 45.2 | 51.9 | 51.7 | 44.5 | 53.7 | 54.8 |
| C2 = -C3 = sel, % | 40.9 | 46.4 | 54.1 | 39.7 | 45.6 | 50.3 | 39.6 | 45.5 | 49.6 | 40.1 | 46.2 | 51.7 |
| n-heptane conv, % | 72.2 | 90.2 | 99.8 | 91.0 | 99.2 | 99.8 | 91.7 | 99.0 | 100.0 | 87.2 | 97.3 | 100.0 |
| C2-C5P | 22.5 | 22.6 | 15.4 | 28.2 | 22.4 | 13.6 | 27.4 | 21.3 | 12.4 | 26.1 | 21.5 | 12.8 |
| C6-C9 NA | 3.5 | 5.0 | 8.2 | 4.5 | 7.3 | 11.4 | 5.2 | 8.1 | 12.6 | 4.5 | 6.9 | 11.4 |
| Aromatics | 4.2 | 5.4 | 9.3 | 8.4 | 10.2 | 13.6 | 8.7 | 10.5 | 14.5 | 7.3 | 8.9 | 13.0 |

Example 8

Procedure for methanol conversion tests. A catalyst loading of 325 mg sized to 40×60 mesh is first pretreated at 500° C. in a flowing $N_2$ for 30 minutes. The catalytic performance is evaluated at one atmosphere pressure and a constant temperature of 450° C. with a constant $N_2$ flow at 135 ml/minute passing through a methanol saturator controlled at 15° C. GC method is set up to capture light paraffin and olefin, benzene, toluene, xylene isomers/ethylbenzene and heavier aromatics.

As shown in Table 8, during methanol conversion, MFIs of the instant invention in the calcined state have consistently higher initial ethylene and aromatics versus comparative examples, despite having in general lower total olefin ($C2=$-$C5=$). Among the Examples of the instant invention, $C_2$-$C_5$ olefin yields increase and the stability improves with increased Si/Al ratios. However, total $C_2$-$C_5$ olefin yields and the total olefin stability are in general no better than those of comparative examples. Conversely, upon steaming, MFIs of the instant invention exhibited higher total olefin ($C_2^=$-$C_5^=$) selectivity with comparable lighter olefins ($C_2^=$-$C_3^=$), aromatics, along with comparable to higher ethylene yields and activity for hydrocarbons formation as shown in Table 9. Furthermore, the stability is vastly improved. The performance is further illustrated in FIGS. 27-41. For MFIs of the instant invention, the stability of methanol conversion to lighter olefins (C2-C3) reaction improves as $SiO_2/Al_2O_3$ ratios increase or with hydrothermal (steam) treatments, and the MFIs of the instant invention at high $SiO_2/Al_2O_3$ (by 160 or higher) or after hydrothermal treatment have comparable stability and C2-C3 olefin yield in MTO reaction to that of comparative examples.

The same observation on stability improvement is also found on the conversion of methanol to aromatics (MTA) in the same evaluation test, but samples showed difference on aromatic yield. As shown in FIGS. 34 to 37, the MTA reaction by MFIs of the instant invention becomes stable as $SiO_2/Al_2O_3$ ratios increase or after the samples are subject to hydrothermal treatment, but the amounts of aromatics exceed those of comparative examples at high $SiO_2/Al_2O_3$ (by 160 or higher) or at medium-to-high $SiO_2/Al_2O_3$ (above 80) after hydrothermal treatment. Among the aromatics produced, the amounts of xylenes produced by MFIs of the instant invention are higher and strikingly contain a significantly higher proportion of para-xylene above about 60% of xylenes as shown in FIGS. 38-41. The increasing participation of active sites in tortuous via straight channels controlling the location of active sites and by reducing carbonaceous deposition at the interactions may result in the desirable stable para-xylene production.

TABLE 8

EDA/TPA MFIs vs. TPA-MFI (580° C. calcination) - Methanol to Olefin and Aromatics

|  | Example 1 | | comparative EX 1.1 | | Example 2 | | comparative EX 2.1 | | Example 3 | | comparative EX 3.1 | |
| --- | --- | --- | --- | --- | --- | --- | --- | --- | --- | --- | --- | --- |
| HOS | 1.2 | 5.3 | 1.2 | 5.3 | 1.2 | 5.3 | 1.2 | 5.3 | 1.2 | 5.3 | 1.2 | 5.3 |
| MeOh | 0.0 | 23.6 | 0.0 | 0.0 | 2.9 | 14.2 | 0.0 | 0.0 | 0.1 | 0.4 | 0.0 | 0.0 |
| DME | 0.0 | 72.1 | 0.0 | 0.0 | 1.0 | 23.9 | 0.0 | 0.0 | 0.0 | 0.0 | 0.0 | 0.0 |
| C1 | 5.8 | 1.7 | 2.3 | 3.6 | 4.7 | 4.1 | 0.4 | 0.7 | 1.3 | 1.7 | 0.4 | 0.5 |
| C2 = | 16.2 | 0.5 | 13.6 | 14.6 | 13.0 | 7.6 | 10.1 | 10.2 | 9.6 | 9.4 | 5.0 | 6.0 |
| C3 = | 29.0 | 0.2 | 17.4 | 18.5 | 31.8 | 19.5 | 44.6 | 44.4 | 44.2 | 42.6 | 47.8 | 46.7 |
| C2-C5 = | 58.7 | 0.6 | 42.8 | 44.3 | 64.9 | 41.1 | 79.3 | 78.3 | 78.6 | 77.0 | 80.5 | 79.0 |
| NA unknown | 2.1 | 0.0 | 2.3 | 2.9 | 7.3 | 6.4 | 4.4 | 4.2 | 5.1 | 6.4 | 5.4 | 5.1 |
| C2-C5P | 12.2 | 0.0 | 31.4 | 28.6 | 7.8 | 4.3 | 14.4 | 14.0 | 10.4 | 9.7 | 12.5 | 13.8 |
| Aromatics | 21.3 | 0.3 | 21.2 | 20.6 | 11.1 | 6.6 | 1.5 | 2.7 | 4.3 | 4.4 | 0.9 | 1.5 |

TABLE 9

EDA/TPA MFIs vs. TPA-MFI (40% steam/650° C.) - Methanol to Olefin and Aromatics

|  | Example 1 | | comparative EX 1.1 | | Example 2 | | Example 3 | | comparative EX 3.1 | |
| --- | --- | --- | --- | --- | --- | --- | --- | --- | --- | --- |
| HOS | 1.2 | 5.3 | 1.2 | 5.3 | 1.2 | 5.3 | 1.2 | 5.3 | 1.2 | 5.3 |
| MeOh | 3.3 | 1.5 | 1.9 | 0.1 | 0.4 | 0.1 | 0.5 | 0.6 | 5.7 | 6.5 |
| DME | 0.9 | 0.2 | 0.4 | 0.0 | 0.0 | 0.0 | 0.0 | 0.0 | 2.6 | 3.0 |
| C1 | 2.4 | 1.9 | 0.8 | 0.6 | 2.9 | 2.6 | 0.5 | 0.4 | 0.3 | 0.3 |
| C2 = | 10.6 | 10.5 | 10.4 | 11.3 | 13.1 | 13.1 | 6.0 | 5.7 | 4.8 | 4.6 |
| C3 = | 32.0 | 33.4 | 29.4 | 28.3 | 34.2 | 34.4 | 41.3 | 41.1 | 39.3 | 38.6 |
| C2 = -C3 = | 42.6 | 43.9 | 39.8 | 39.6 | 47.3 | 47.5 | 47.3 | 46.8 | 44.1 | 43.2 |
| C2 = -C5 = | 63.8 | 65.4 | 57.2 | 54.5 | 67.3 | 67.3 | 72.3 | 71.7 | 70.4 | 69.0 |
| NA unknown | 9.4 | 8.6 | 8.9 | 7.8 | 5.9 | 5.1 | 7.8 | 8.3 | 11.9 | 12.2 |
| C2-C5P | 12.1 | 13.0 | 23.2 | 26.5 | 13.3 | 13.8 | 14.5 | 14.4 | 8.0 | 7.7 |
| Aromatics | 7.5 | 9.1 | 7.3 | 10.1 | 10.0 | 10.8 | 4.0 | 4.1 | 0.9 | 0.9 |

To further illustrate the utility of active sites located in the constrained environment, the methanol conversion test is modified to obtained performance at earlier times on stream comparable to contact times representative of processes such as fluidized beds, riser and etc. The modified methanol conversion test involves the same 500° C., 30-minutes $N_2$ pretreatment procedure and measures performances at temperatures of 450° C. Methanol feed is still introduced via flowing $N_2$ at 135 ml/minute through a saturator of liquid normal heptane controlled at 15° C., but the catalyst is only exposed to methanol vapor feed for 5 minutes before GC sampling of product and flow is switched to pure $N_2$ immediately afterwards, and catalyst stays in pure $N_2$ flow at 135 ml/min during transition to the next sampling and GC injection. The contact in the modified methanol conversion test corresponds to a catalyst to feed ratios on a wight basis from about 1 to about 10. As shown in Table 10, example MFIs of the instant invention made using zeolite LTA as the aluminum source gave stable methanol conversion activity, higher total olefin, higher ethylene, higher propylene, comparable methane but lower aromatics and lower C2-C5 paraffin in comparison with comparative example MFIs made using liquid sodium aluminate.

TABLE 10

Modified Methanol Conversion Tests of LTA-MFIs

|  | Example 5.1 | | Example 5.2 | | Comparative Ex. 5.4 | | Comparative Ex. 5.5 | |
| --- | --- | --- | --- | --- | --- | --- | --- | --- |
| HOS | 1.4 | 6.9 | 1.4 | 6.9 | 1.4 | 6.9 | 1.4 | 6.9 |
| MeOH | 0.0 | 0.0 | 0.0 | 0.1 | 0.0 | 0.0 | 0.0 | 0.0 |
| DME | 0.0 | 0.0 | 0.0 | 0.0 | 0.0 | 0.0 | 0.0 | 0.0 |
| C1 | 1.3 | 1.6 | 1.2 | 1.7 | 0.8 | 1.3 | 0.9 | 2.1 |
| C2= | 18.1 | 18.2 | 16.1 | 15.6 | 14.9 | 14.3 | 14.0 | 13.4 |
| C3= | 23.8 | 23.8 | 23.8 | 24.0 | 19.1 | 18.4 | 18.2 | 17.5 |
| C2-C5= | 55.3 | 54.9 | 52.4 | 52.2 | 46.6 | 44.7 | 44.6 | 42.8 |
| NA unknown | 2.0 | 2.0 | 2.2 | 2.5 | 2.2 | 2.5 | 2.6 | 2.5 |
| C2-C5P | 25.4 | 25.3 | 27.8 | 27.0 | 31.9 | 31.6 | 32.7 | 32.1 |
| Aromatics | 15.8 | 16.0 | 16.2 | 16.2 | 18.4 | 19.8 | 19.0 | 20.5 |

Example 9

DFT calculations were carried out in the Vienna ab initio Simulation Package (G. Kresse and J. Hafner, "Ab initio molecular dynamics for liquid metals", Phys. Rev. B, 47, 558 (1993); G. Kresse and J. Furthmüller, "Efficiency of ab-initio total energy calculations for metals and semiconductors using a plane-wave basis set", Comput. Mat. Sci., 6, 15 (1996)). The MFI framework was modeled by a supercell of 20.09 Å×17.74 Å×13.14 Å with 192 O and 96 Si atoms. The acid site was created by replace one Si atom with Al. The PBE density functional (J. P. Perdew, K. Burke, and M. Ernzerhof, "Generalized gradient approximation made simple", Phys. Rev. Lett., 77, 3865 (1996)) with the Van der Waals correction in the D2 method of Grimme (S. Grimme, "Semiempirical GGA-type density functional constructed with a long-range dispersion correction", J. Comp. Chem., 27, 1787 (2006)) was used to model electronic exchange and correlation. Vanderbilt pseudo-potentials constructed within the projected augmented wave framework were used for core electrons (G. Kresse and D. Joubert, "From ultrasoft pseudopotentials to the projector augmented-wave method", Phys. Rev. B, 59, 1758 (1999)), with a plane wave basis set with an energy cutoff of 400 eV for the valence electrons, implemented in a 1×1×1 k-point sampling of the Brillouin zone that is be sufficient. Geometry optimization was considered converged when the force dropped below 0.01 eV/A on each atom. A Gaussian type of smearing in the amount of 0.05 eV was applied to speed up the convergence in the electronic state optimization. The projection operators are evaluated in real-space, with fully automatic optimization of projection operators. The adsorption (or binding) energy, $E_{ads}$, for a xylene molecule on a site is calculated as follows in Eq. 1.

$$E_{ads} = E_{(xylene/surface)} - E_{(surface)} - E_{(xylene)} \quad \text{Equation 1:}$$

The diffusion pathway was optimized with the nudged elastic band method (G. Henkelman and H. Jonsson, "Improved tangent estimate in the nudged elastic band method for finding minimum energy paths and saddle points", J. Chem. Phys., 113, 9978 (2000)) with a force tolerance of 0.01 eV/Å. The diffusion barrier is calculated as the energy gap between the transition state of diffusion with the highest energy and the adsorption state with the lowest energy along the diffusion pathway. Results of the calculation is listed in Table 2 previously.

SPECIFIC EMBODIMENTS

While the following is described in conjunction with specific embodiments, it will be understood that this description is intended to illustrate and not limit the scope of the preceding description and the appended claims.

A first embodiment of the invention is an improved MFI zeolite composition in the calcined and ion-exchanged form comprising a $SiO_2/Al_2O_3$ ratio of from about 60 to about 600 and having low aluminum occupation at intersection sites characterized by an ortho-xylene to para-xylene uptake ratio of no less than 0.1 and no more than about 0.55. The ortho-xylene to para-xylene uptake ratio of no less than 0.1 and no more than about 0.50. An embodiment of the invention is one, any or all of prior embodiments in this paragraph up through the first embodiment in this paragraph wherein the ortho-xylene to para-xylene uptake ratio is less than about 0.4. An embodiment of the invention is one, any or all of prior embodiments in this paragraph up through the first embodiment in this paragraph wherein the ortho-xylene to para-xylene uptake ratio is less than about 0.3. An embodiment of the invention is one, any or all of prior embodiments in this paragraph up through the first embodiment in this paragraph further comprising a micropore volume as determined by $N_2$ BET of from about 0.11 mL/g to about 0.135 mL/g. An embodiment of the invention is one, any or all of prior embodiments in this paragraph up through the first embodiment in this paragraph wherein the $SiO_2/Al_2O_3$ ratio is from about 90 to about 600. An embodiment of the invention is one, any or all of prior embodiments in this paragraph up through the first embodiment in this paragraph further comprising post-synthetic hydrothermally treatment at temperature of from about 650° C. to about 800° C. at about 40 to 100% steam for a time of about 12 to about 20 hours. An embodiment of the invention is one, any or all of prior embodiments in this paragraph up through the first embodiment in this paragraph further characterized by a heptane conversion of greater than about 10 wt % and a selectivity to ethylene and propylene of greater than about 40 wt % in the modified paraffin cracking test. An embodiment of the invention is one, any or all of prior embodiments in this paragraph up through the first embodiment in this paragraph further characterized by an ethylene molar percentage of greater than 40% out of the combined ethylene, propylene and butylenes formed in the modified paraffin cracking test. An embodiment of the invention is one, any or all of prior embodiments in this paragraph up through the first embodiment in this paragraph further characterized by a selectivity to ethylene and propylene of greater than about 5% in the modified paraffin cracking test wherein the hydrothermal treatment temperature was greater than about 750° C. An embodiment of the invention is one, any or all of prior embodiments in this paragraph up through the first embodiment in this paragraph further characterized by an ethylene to light olefin ratio of greater than 0.4 in the modified paraffin cracking test. An embodiment of the invention is one, any or all of prior embodiments in this paragraph up through the first embodiment in this paragraph further comprising formulating the improved MFI zeolite into a catalyst via a forming process comprising extrusion, pelletization, marumerization, oil dropping, spray drying, and mixtures thereof.

A second embodiment of the invention is a process for conversion of hydrocarbon to product comprising contacting a feedstream comprising hydrocarbon with a catalyst; converting the feedstream to a product at reaction conditions, and recovering a product comprising light olefins, aromatics, or mixtures thereof, wherein the catalyst comprises an improved MFI zeolite comprising in the calcined and ion-exchanged form a $SiO_2/Al_2O_3$ ratio of from about 60 to about 600, and having low aluminum occupation at intersection sites characterized by an ortho-xylene to para-xylene uptake ratio of no less than 0.1 and no more than about 0.55. An embodiment of the invention is one, any or all of prior embodiments in this paragraph up through the first embodiment in this paragraph wherein the product comprises one or more xylenes. An embodiment of the invention is one, any or all of prior embodiments in this paragraph up through the first embodiment in this paragraph wherein the product comprises para-xylene. An embodiment of the invention is one, any or all of prior embodiments in this paragraph up through the first embodiment in this paragraph wherein the para-xylene is greater than about 24% of the xylenes. An embodiment of the invention is one, any or all of prior embodiments in this paragraph up through the first embodiment in this paragraph wherein the improved MFI zeolite further comprises a micropore volume as determined by $N_2$ BET of from about 0.11 mL/g to about 0.135 mL/g. An embodiment of the invention is one, any or all of prior embodiments in this paragraph up through the first embodiment in this paragraph wherein the product comprises ethylene and propylene. An embodiment of the invention is one, any or all of prior embodiments in this paragraph up through the first embodiment in this paragraph wherein the feedstream comprises a diluent selected from the group consisting of nitrogen, steam, methane, ethane, hydrogen, and mixtures thereof. An embodiment of the invention is one, any or all of prior embodiments in this paragraph up through the first embodiment in this paragraph wherein the hydrocarbon comprises naphtha. An embodiment of the invention is one, any or all of prior embodiments in this paragraph up through the first embodiment in this paragraph wherein the hydrocarbon comprises vacuum gas oil. An embodiment of the invention is one, any or all of prior embodiments in this paragraph up through the first embodiment in this paragraph wherein the contacting occurs in a fluidized bed reactor. An embodiment of the invention is one, any or all of prior embodiments in this paragraph up through the first embodiment in this paragraph wherein the ortho-xylene to para-xylene uptake ratio is less than about 0.4. An embodiment of the invention is one, any or all of prior embodiments in this paragraph up through the first embodiment in this paragraph wherein the ortho-xylene to para-xylene uptake ratio is less than about 0.3.

A third embodiment of the invention is a process for conversion of oxygenate to product comprising contacting a feedstream comprising oxygenate with a catalyst; converting the feedstream to a product at reaction conditions, and recovering a product comprising light olefins, aromatics, or mixtures thereof, wherein the catalyst comprises an improved MFI zeolite comprising in the calcined and ion-exchanged form a $SiO_2/Al_2O_3$ ratio of from about 60 to about 600, and having low aluminum occupation at intersection sites characterized by an ortho-xylene to para-xylene uptake ratio of no less than 0.1 and no more than about 0.55. An embodiment of the invention is one, any or all of prior embodiments in this paragraph up through the second embodiment in this paragraph wherein the product comprises one or more xylenes. An embodiment of the invention is one, any or all of prior embodiments in this paragraph up through the second embodiment in this paragraph wherein the product comprises para-xylene. An embodiment of the invention is one, any or all of prior embodiments in this paragraph up through the second embodiment in this paragraph wherein the para-xylene is greater than about 24% of the xylenes. An embodiment of the invention is one, any or all of prior embodiments in this paragraph up through the second embodiment in this paragraph wherein the product comprises ethylene and propylene. An embodiment of the invention is one, any or all of prior embodiments in this paragraph up through the second embodiment in this paragraph wherein the feedstream comprises a diluent selected from the group consisting of nitrogen, steam, methane, ethane, hydrogen, and mixtures thereof. An embodiment of the invention is one, any or all of prior embodiments in this paragraph up through the second embodiment in this paragraph wherein the contacting occurs in a fluidized bed reactor. An embodiment of the invention is one, any or all of prior embodiments in this paragraph up through the second embodiment in this paragraph wherein the oxygenate comprises methanol. An embodiment of the invention is one, any or all of prior embodiments in this paragraph up through the second embodiment in this paragraph wherein the ortho-xylene to para-xylene uptake ratio is less than about 0.4. An embodiment of the invention is one, any or all of prior embodiments in this paragraph up through the second embodiment in this paragraph wherein the ortho-xylene to para-xylene uptake ratio is less than about 0.3. An embodiment of the invention is one, any or all of prior embodiments in this paragraph up through the second embodiment in this paragraph wherein the improved MFI zeolite further comprises a micropore volume as determined by $N_2$ BET of from about 0.11 mL/g to about 0.135 mL/g.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for conversion of oxygenate to product comprising:
    contacting a feedstream comprising an oxygenate with a catalyst;
    converting the feedstream to a product at reaction conditions; and
    recovering a product comprising light olefins, aromatics, or mixtures thereof,
    wherein the catalyst comprises an improved MFI zeolite comprising in the calcined and ion-exchanged form a $SiO_2/Al_2O_3$ ratio of from about 60 to about 600 and a Si/B ratio of from about 2 to about 50, and having low aluminum occupation at intersection sites characterized by an ortho-xylene to para-xylene uptake ratio of no less than 0.1 and no more than about 0.55.

2. The process of claim 1 wherein the product comprises one or more xylenes.

3. The process of claim 1 wherein the product comprises ethylene and propylene.

4. The process of claim 1 wherein the feedstream comprises a diluent selected from the group consisting of nitrogen, steam, methane, ethane, hydrogen, and mixtures thereof.

5. The process of claim 1 wherein the contacting occurs in a fluidized bed reactor.

6. The process of claim 1 wherein the oxygenate comprises methanol.

7. The process of claim 1 wherein the improved MFI zeolite further comprises a micropore volume as determined by $N_2$ BET of from about 0.11 mL/g to about 0.135 mL/g.

* * * * *